(12) United States Patent
Kawashima et al.

(10) Patent No.: US 8,445,529 B2
(45) Date of Patent: May 21, 2013

(54) INDOLE DERIVATIVE HAVING, CARBAMOYL GROUP, UREIDO GROUP AND SUBSTITUTED OXY GROUP

(75) Inventors: Kenji Kawashima, Ikoma (JP); Hiroshi Enomoto, Ikoma (JP); Minoru Yamamoto, Ikoma (JP); Masaaki Murai, Ikoma (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 25 days.

(21) Appl. No.: 13/054,041

(22) PCT Filed: Jul. 14, 2009

(86) PCT No.: PCT/JP2009/062698
§ 371 (c)(1),
(2), (4) Date: Jan. 31, 2011

(87) PCT Pub. No.: WO2010/007972
PCT Pub. Date: Jan. 21, 2010

(65) Prior Publication Data
US 2011/0124668 A1    May 26, 2011

(30) Foreign Application Priority Data
Jul. 14, 2008  (JP) .................................. 2008-182147

(51) Int. Cl.
*A61K 31/404* (2006.01)
*C07D 209/40* (2006.01)
(52) U.S. Cl.
USPC .......................................... 514/419; 548/483
(58) Field of Classification Search .... 548/483; 514/419
See application file for complete search history.

(56) References Cited

U.S. PATENT DOCUMENTS

| | | |
|---|---|---|
| 2002/0107252 A1 | 8/2002 | Baxter et al. |
| 2003/0229047 A1 | 12/2003 | Joshi-Hangal et al. |
| 2004/0235821 A1 | 11/2004 | Griffiths et al. |
| 2004/0242573 A1 | 12/2004 | Faull et al. |
| 2005/0054631 A1 | 3/2005 | Jiang et al. |
| 2005/0159474 A1 | 7/2005 | Arnould |
| 2005/0203075 A1 | 9/2005 | Agoston et al. |
| 2006/0058522 A1 | 3/2006 | Faull et al. |
| 2006/0111431 A1 | 5/2006 | Morley et al. |
| 2006/0116419 A1 | 6/2006 | Callahan et al. |
| 2007/0208057 A1 | 9/2007 | Zeldis |
| 2007/0275962 A1 | 11/2007 | Koul et al. |
| 2008/0269200 A1 | 10/2008 | Baldwin et al. |
| 2008/0293802 A1 | 11/2008 | Kerns |
| 2010/0041628 A1 | 2/2010 | Enomoto et al. |

FOREIGN PATENT DOCUMENTS

| | | |
|---|---|---|
| WO | WO 96/20191 | 7/1996 |
| WO | WO 96/20196 A1 | 7/1996 |
| WO | WO 01/58890 A1 | 8/2001 |
| WO | WO 2004/009582 A1 | 1/2004 |
| WO | WO 2004/053087 A2 | 6/2004 |
| WO | WO 2005/123745 A1 | 12/2005 |
| WO | WO 2006/036031 A1 | 4/2006 |
| WO | WO 2007/002481 A2 | 1/2007 |
| WO | WO 2008/087933 A1 | 7/2008 |

OTHER PUBLICATIONS

Rheumatoid arthritis [online] retrieved on Aug. 26, 2010 from the internet. URL: http://www.mayoclinic.com/health/rheumatoid-arthritis/DS00020.
Age-related macular degeneration [online] retrieved on Aug. 26, 2010 from the internet. URL: http://www.medicinenet.com/script/main/art.asp?articlekey=10008.
Supplementary European Search Report dated Aug. 17, 2011 for EP 09797897.
A. Kumar, et al, "Nuclear factor-κB: its role in health and disease," J. Mol. Med., 2004, 82, pp. 434-448.
Gazzete Chimica Italiana 48, II, 1918, pp. 151-182, with English translation of p. 170, line 22 to p. 171, line 7.
A. Bingham et al, "A novel series of potent and selective IKK2 inhibitors", Bioorganic & Medicinal Chemistry Letters, 2004, 14, pp. 409-412.
M. Mor et al, "Synthesis, Pharmacological Characterization and QSAR Studies on 2-Substituted Indole Melatonin Receptor Ligands", Bioorganic & Medicinal Chemistry, 2001, 9, pp. 1045-1057.

*Primary Examiner* — Shawquia Young
(74) *Attorney, Agent, or Firm* — Holtz Holtz Goodman & Chick PC

(57) ABSTRACT

An indole compound having a carbamoyl group, a ureido group and a substituted oxy group having the following formula (1) or a salt thereof:

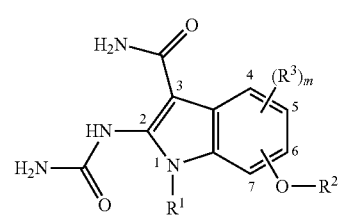

(1)

In the formula (1), $R^1$ represents a hydrogen atom, an alkyl group, a hydroxy group, or an alkoxy group; $R^2$ represents a hydrogen atom, an alkyl group, a cycloalkyl group, an aryl group, or a heterocyclic group; $R^3$ represents a halogen atom, an alkyl group, an alkenyl group, an alkynyl group, a cycloalkyl group, an aryl group, a heterocyclic group an alkoxy group, an alkenyloxy group, an alkynyloxy group, a cycloalkyloxy group, an aryloxy group or a heterocyclic oxy group; m represents 0, 1, 2, or 3.

18 Claims, No Drawings

INDOLE DERIVATIVE HAVING, CARBAMOYL GROUP, UREIDO GROUP AND SUBSTITUTED OXY GROUP

This application is the United States national phase application of International Application PCT/JP2009/062698 filed Jul. 14, 2009.

TECHNICAL FIELD

The present invention relates to a novel indole derivative having a carbamoyl group, a ureido group and a substituted oxy group or a salt thereof which is useful as a pharmaceutical. The derivative or a salt thereof has an inhibitory activity against IKKβ and is therefore useful as a preventive and/or therapeutic agent for a disease considered to be associated with IKKβ.

BACKGROUND ART

Nuclear factor κB (hereinafter referred to as "NF-κB") associated with signaling from the outside of a cell to the inside of a nucleus is a transcription factor associated with expression of many genes induced in immunological/inflammatory reactions. NF-κB which is a transcription factor generally forms a complex with a control protein called IκB and is localized in cytoplasm as an inactive form. When the IκB of the complex is phosphorylated by an enzyme called IKKβ, degradation of IκB is developed. NF-κB that is released due to the IκB degradation becomes active and translocates from the cytoplasm to the nucleus to activate transcription of a target gene, thereby enhancing production of cytokines such as tumor necrosis factor (hereinafter referred to as "TNF"), interleukin-1 (hereinafter referred to as "IL-1"), and interleukin-6 (hereinafter referred to as "IL-6") or cell proliferation.

Therefore, it is possible to inhibit activation of NF-κB by way of control of IKKβ, which makes it possible to suppress the production of cytokines such as TNF, IL-1, IL-6 and the like, or the cell proliferation, thereby realizing prevention and/or treatment of diseases considered to be associated with the factors.

Various diseases such as rheumatoid arthritis, asthma, diabetes, and cancer have been known as the diseases considered to be associated with IKKβ (Journal of Molecular Medicine, 82, 434-448 (2004), WO 06/036031).

As compounds having an IKKβ inhibitory activity, condensed furan derivatives disclosed in WO 06/036031, aromatic heterocyclic 5-membered ring carboxamide derivatives disclosed in WO 01/58890, substituted thiophenecarboxamide derivatives disclosed in WO 04/009582, and the like have been known.

Compounds having a urea structure at the 2-position of an indole ring are disclosed in Gazzete Chimica Italiana 48, II, 151-182 (1918), and compounds having an amide structure at the 3-position of an indole ring are disclosed in WO 96/020191. However, these publications do not contain any specific disclosure nor suggestion of compounds having a ureido group at the 2-position and a carbamoyl group at the 3-position of an indole ring, and having a substituted oxy group on benzene ring part of an indole ring. Furthermore it is not mentioned about the IKKβ inhibitory effect of these compounds at all.

DISCLOSURE OF THE PRESENT INVENTION

Problems to be Solved

It is a very interesting subject to study of the synthesis of a novel indole derivative having a carbamoyl group, a ureido group and a substituted oxy group or a salt, and to find a pharmacological action of the derivative or a salt thereof.

Means for Solving the Problem

The inventors conducted the synthesis of novel indole derivatives having a carbamoyl group, a ureido group and a substituted oxy group or a salt thereof and succeeded in creating many novel compounds.

As a result of the study on pharmacological action of the derivative or a salt thereof, the inventors found that the derivative or a salt thereof has the IKKβ inhibitory activity and is useful as a pharmaceutical, thereby accomplishing the present invention.

More specifically, the present invention relates to a compound represented by the following general formula (1) or a salt thereof (hereinafter referred to as "the present compound") and a pharmaceutical composition comprising at least one compound of the present compound. Also, a preferred invention for medicinal use relates to an IKKβ inhibitor, and examples of a target disease of the IKKβ inhibitor include diseases considered to be associated with IKKβ, such as an inflammatory disease, an autoimmune disease, an allergic disease, an infectious disease, a degenerative disease, a vascular disease, a nerve/sensory organ disease, an endocrine/metabolic disease, a neoplastic disease, a congenital disease, a traumatic disease, and an adverse reaction after organ transplantation, and more specific examples of such diseases include keratitis, conjunctivitis, uveitis, osteoarthritis, chronic obstructive pulmonary disease, bronchitis, pneumonia, hepatitis, pancreatitis, nephritis, sepsis, systemic inflammatory response syndrome, rheumatoid arthritis, psoriasis, multiple sclerosis, Crohn's disease, ulcerative colitis, systemic erythematosus, Sjogren's syndrome, multiple myositis, dermatomyositis, asthma, allergic rhinitis, hives, atopic dermatitis, age-related macular degeneration, retinopathy of prematurity, polypoidal choroidal vasculopathy, retinal vein occlusion, diabetes and its complication (diabetic retinopathy, diabetic macular edema, diabetic neuropathy, diabetic nephropathy), leukemia, multiple myeloma, malignant lymphoma, solid cancer, cachexia, Alzheimer's disease, Parkinson's syndrome, cerebral infarction, cerebral apoplexy, glaucoma, acquired immune deficiency syndrome, osteoporosis, obesity, fibrosis, gout, fever, headache, acute/chronic pain, hypertension, hyperlipidemia, arteriosclerosis, cardiac infarct, angina, dystrophia, acute respiratory distress syndrome, and the like.

A particularly preferred invention for medicinal use relates to a preventive and/or therapeutic agent for the above diseases, comprising at least one compound of the present compound as an active ingredient.

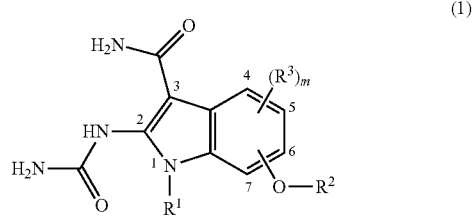

(1)

[wherein $R^1$ represents a hydrogen atom, a lower alkyl group which may have a substituent, a hydroxy group, or a lower alkoxy group which may have a substituent;

$R^2$ represents a hydrogen atom, a lower alkyl group which may have a substituent, a lower cycloalkyl group which may have a substituent, an aryl group which may have a substituent, or a heterocyclic group which may have a substituent;

$R^3$ represents a halogen atom, a lower alkyl group which may have a substituent, a lower alkenyl group which may have a substituent, a lower alkynyl group which may have a substituent, a lower cycloalkyl group which may have a substituent, an aryl group which may have a substituent, a heterocyclic group which may have a substituent, a lower alkoxy group which may have a substituent, a lower alkenyloxy group which may have a substituent, a lower alkynyloxy group which may have a substituent, a lower cycloalkyloxy group which may have a substituent, an aryloxy group which may have a substituent, or a heterocyclic oxy group which may have a substituent;

m represents 0, 1, 2, or 3, provided that $R^3$ may be the same or different when m is 2 or 3. Hereinafter the same shall apply]

Advantageous Effect of the Present Invention

The present invention provides a novel indole derivative having a carbamoyl group, a ureido group and a substituted oxy group or a salt thereof. The present compound has an excellent IKKβ inhibitory activity and is useful as an IKKβ inhibitor. Particularly, the present compound is useful as a preventive and/or therapeutic agent for a disease considered to be associated with IKKβ, such as an inflammatory disease, an autoimmune disease, an allergic disease, an infectious disease, a degenerative disease, a vascular disease, a nerve/sensory organ disease, an endocrine/metabolic disease, a neoplastic disease, a congenital disease, a traumatic disease, or an adverse reaction after organ transplantation, and more specific examples of such diseases include keratitis, conjunctivitis, uveitis, osteoarthritis, chronic obstructive pulmonary disease, bronchitis, pneumonia, hepatitis, pancreatitis, nephritis, sepsis, systemic inflammatory response syndrome, rheumatoid arthritis, psoriasis, multiple sclerosis, Crohn's disease, ulcerative colitis, systemic erythematosus, Sjogren's syndrome, multiple myositis, dermatomyositis, asthma, allergic rhinitis, hives, atopic dermatitis, age-related macular degeneration, retinopathy of prematurity, polypoidal choroidal vasculopathy, retinal vein occlusion, diabetes and its complication (diabetic retinopathy, diabetic macular edema, diabetic neuropathy, diabetic nephropathy), leukemia, multiple myeloma, malignant lymphoma, solid cancer, cachexia, Alzheimer's disease, Parkinson's syndrome, cerebral infarction, cerebral apoplexy, glaucoma, acquired immune deficiency syndrome, osteoporosis, obesity, fibrosis, gout, fever, headache, acute/chronic pain, hypertension, hyperlipidemia, arteriosclerosis, cardiac infarct, angina, dystrophia, acute respiratory distress syndrome, and the like.

BEST MODE FOR CARRYING OUT THE PRESENT INVENTION

Hereinafter, definitions of terms and phrases (atoms, groups, rings, and the like) to be used in this specification will be described in detail. Further, when other definitions of terms and phrases are applied to the definitions of terms and phrases mentioned below, preferred ranges of the respective definitions can also be applied.

The term "halogen atom" means a fluorine, chlorine, bromine, or iodine atom.

The term "lower alkyl group" means a straight-chain or branched alkyl group having 1 to 8, preferably 1 to 6, carbon atoms. Specific examples thereof include methyl, ethyl, n-propyl, n-butyl, n-pentyl, n-hexyl, n-heptyl, n-octyl, isopropyl, isobutyl, sec-butyl, tert-butyl, and isopentyl groups and the like.

The term "lower alkenyl group" means a straight-chain or branched alkenyl group having 2 to 8, preferably 2 to 6, carbon atoms. Specific examples thereof include vinyl, propenyl, butenyl, pentenyl, hexenyl, heptenyl, octenyl, isopropenyl, 2-methyl-1-propenyl, and 2-methyl-2-butenyl groups and the like.

The term "lower alkynyl group" means a straight-chain or branched alkynyl group having 2 to 8, preferably 2 to 6, carbon atoms. Specific examples thereof include ethynyl, propynyl, butynyl, pentynyl, hexynyl, heptynyl, octynyl, isobutynyl, and isopentynyl groups and the like.

The term "lower cycloalkyl group" means a cycloalkyl group having 3 to 8, preferably 3 to 6, carbon atoms. Specific examples thereof include cyclopropyl, cyclobutyl, cyclopentyl, cyclohexyl, cycloheptyl, or cyclooctyl group.

The term "aryl group" means a residue formed by removing one hydrogen atom from a monocyclic aromatic hydrocarbon group having 6 to 14 carbon atoms or a bicyclic or tricyclic condensed polycyclic aromatic hydrocarbon. Specific examples thereof include phenyl, naphthyl, anthryl, and phenanthryl groups and the like.

The term "heterocyclic ring" means a saturated or unsaturated monocyclic heterocyclic ring or a bicyclic or tricyclic condensed polycyclic heterocyclic ring having in the ring one or a plurality of hetero atoms selected from nitrogen atoms, oxygen atoms, sulfur atoms, and boron atoms.

Specific examples of the saturated monocyclic heterocyclic ring include those having a nitrogen atom in a ring such as aziridine, azetidine, pyrrolidine, pyrazolidine, imidazolidine, triazolidine, piperidine, hexahydropyridazine, hexahydropyrimidine, piperazine, homopiperidine, and homopiperazine, those having an oxygen atom in a ring such as tetrahydrofuran, tetrahydropyran, [1,4]dioxane, and [1,2]dioxirane, those having a sulfur atom in a ring such as tetrahydrothiophene, tetrahydrothiopyran, and dithiolane, those having a nitrogen atom and an oxygen atom in a ring such as oxazolidine, isooxazolidine, and morpholine, those having a nitrogen atom and a sulfur atom in a ring such as thiazolidine, isothiazolidine, and thiomorpholine, those having an oxygen atom and a born atom in a ring such as dioxaborane, and the like.

Each of the saturated monocyclic heterocyclic rings may be condensed with a benzene ring or the like to form a bicyclic or tricyclic condensed polycyclic heterocyclic ring such as dihydroindole, dihydroindazole, dihydrobenzimidazole, tetrahydroquinoline, tetrahydroisoquinoline, tetrahydrocinnoline, tetrahydrophthalazine, tetrahydroquinazoline, tetrahydroquinoxaline, dihydrobenzofuran, dihydroisobenzofuran, chromane, isochromane, benzo[1,3]dioxole, 2,3-dihydrobenzo[1,4]dioxin, dihydrobenzothiophene, dihydroisobenzothiophene, thiochromane, isothiochromane, dihydrobenzoxazole, dihydrobenzisooxazole, dihydrobenzoxazine, dihydrobenzothiazole, dihydrobenzisothiazole, dihydrobenzothiazine, xanthene, 4a-carbazole, perimidine, or the like.

Specific examples of the unsaturated monocyclic heterocyclic ring include those having a nitrogen atom in a ring such as dihydropyrrole, pyrrole, dihydropyrazole, pyrazole, dihydroimidazole, imidazole, dihydrotriazole, triazole, tetrahydropyridine, dihydropyridine, pyridine, tetrahydropyridazine, dihydropyridazine, pyridazine, tetrahydropyrimidine, dihydropyrimidine, pyrimidine, tetrahydropyrazine, dihydropyrazine, and pyrazine, those having an oxygen atom in a ring such as dihydrofuran, furan, dihydropyran, and pyran, those having a sulfur atom in a ring such as dihydrothiophene, thiophene, dihydrothiopyran, and thiopyran, those having a nitrogen atom and an oxygen atom in a ring such as dihydrooxazole, oxazole, dihydroisooxazole, isooxazole, dihydrooxazine, and oxazine, those having a nitrogen atom and a sulfur atom in a ring such as dihydrothiazole, thiazole, dihydroisothiazole, isothiazole, dihydrothiazine, and thiazine, and the like.

Each of the unsaturated monocyclic heterocyclic rings may be condensed with a benzene ring or the like to form a bicyclic or tricyclic condensed polycyclic heterocyclic ring such as indole, indazole, benzimidazole, benzotriazole, dihydroquinoline, quinoline, dihydroisoquinoline, isoquinoline, phenanthridine, dihydrocinnoline, cinnoline, dihydrophthalazine, phthalazine, dihydroquinazoline, quinazoline, dihydroquinoxaline, quinoxaline, benzofuran, isobenzofuran, chromene, isochromene, benzothiophene, isobenzothiophene, thiochromene, isothiochromene, benzoxazole, benzisoxazole, benzoxazine, benzothiazole, 4,5,6,7-tetrahydrobenzothiazole, benzisothiazole, benzothiazine, phenoxanthine, carbazole, β-carboline, phenanthridine, acridine, phenanthroline, phenazine, phenothiazine, phenoxazine, or the like.

Further, in each of these heterocyclic rings, when the heterocyclic ring has two hydrogen atoms on an identical carbon atom, the hydrogen atoms may be substituted by an oxo group to form heterocyclic ketone such as 2-pyrrolidone, 4-piperidone, 4-thiazolidone, pyran-4-(4H)-one, pyrazine-2-(3H)-one, or the like, and such heterocyclic ketones are encompassed in the scope of the heterocyclic ring of the present invention.

The term "heterocyclic group" means a residue formed by removing one hydrogen atom from a heterocyclic ring. Specific examples thereof are given by applying the above definition of heterocyclic ring to heterocyclic group.

The term "lower alkoxy group" means a group in which the hydrogen atom of a hydroxy group is substituted by a lower alkyl group. Specific examples thereof include methoxy, ethoxy, n-propoxy, n-butoxy, n-pentyloxy, n-hexyloxy, n-heptyloxy, n-octyloxy, isopropoxy, isobutoxy, sec-butoxy, tert-butoxy, and isopentyloxy groups and the like.

The term "lower alkenyloxy group" means a group in which the hydrogen atom of a hydroxy group is substituted by a lower alkenyl group. Specific examples thereof include vinyloxy, propenyloxy, butenyloxy, pentenyloxy, hexenyloxy, heptenyloxy, octenyloxy, isopropenyloxy, 2-methyl-1-propenyloxy and 2-methyl-2-butenyloxy groups and the like.

The term "lower alkynyloxy group" means a group in which the hydrogen atom of a hydroxy group is substituted by a lower alkynyl group. Specific examples thereof include ethynyloxy, propynyloxy, butynyloxy, pentynyloxy, hexynyloxy, heptynyloxy, octynyloxy, isobutynyloxy and isopentynyloxy groups and the like.

The term "lower cycloalkyloxy group" means a group in which the hydrogen atom of a hydroxy group is substituted by a lower cycloalkyl group. Specific examples thereof include cyclopropyloxy, cyclobutyloxy, cyclopentyloxy, cyclohexyloxy, cycloheptyloxy, and cyclooctyloxy groups and the like.

The term "aryloxy group" means a group in which the hydrogen atom of a hydroxy group is substituted by an aryl group. Specific examples thereof include phenoxy, naphthoxy, anthryloxy, and phenanthryloxy groups and the like.

The term "heterocyclic oxy group" means a group in which the hydrogen atom of a hydroxy group is substituted by a heterocyclic group. Specific examples thereof are given by applying the above definitions of heterocyclic ring and heterocyclic group to heterocyclic oxy group.

The term "lower alkyl group which may have a substituent", "lower alkenyl group which may have a substituent", "lower alkynyl group which may have a substituent", "lower alkoxy group which may have a substituent", "lower alkenyloxy group which may have a substituent" and/or "lower alkynyloxy group which may have a substituent" mean or means "lower alkyl group", "lower alkenyl group", "lower alkynyl group", "lower alkoxy group", "lower alkenyloxy group" and/or "lower alkynyloxy group" which may have one or a plurality of substituents selected from the group consisting of a halogen atom, a lower cycloalkyl group, an aryl group, a heterocyclic group, a nitro group, a cyano group, —$OR^p$, —$COR^q$, —$COOR^r$, —$CONR^sR^t$, —$NR^uR^v$ and —$NHCOR^w$ (preferably, a lower cycloalkyl group, an aryl group and a heterocyclic group).

The term "lower cycloalkyl group which may have a substituent", "aryl group which may have a substituent", "heterocyclic group which may have a substituent", "lower cycloalkyloxy group which may have a substituent", "aryloxy group which may have a substituent", and/or "heterocyclic oxy group which may have a substituent" mean or means "lower cycloalkyl group", "aryl group", "heterocyclic group", "lower cycloalkyloxy group", "aryloxy group", and/or "heterocyclic oxy group" which may have one or a plurality of substituents selected from the group consisting of a halogen atom, a lower alkyl group, a lower alkenyl group, a lower alkynyl group, a lower cycloalkyl group, an aryl group, a heterocyclic group, a nitro group, a cyano group, —$OR^p$, —$COR^q$, —$COOR^r$, —$CONR^sR^t$, —$NR^uR^v$, and —$NHCOR^w$ (preferably, a halogen atom, a lower alkyl group, a nitro group, —$OR^p$, —$NR^uR^v$, and —$NHCOR^w$)

Wherein, $R^p$, $R^q$, $R^r$, $R^s$, $R^t$, $R^u$, $R^v$, and $R^w$ may be the same or different and each represents a group selected from the group consisting of a hydrogen atom, a lower alkyl group, a lower alkyl group substituted with a lower alkoxy group, a lower alkenyl group, a lower alkynyl group, a lower cycloalkyl group, an aryl group, and a heterocyclic group.

The term "a plurality of substituents" used in the present invention may be the same or different, and the number of the groups may preferably be 2 or 3, particularly preferably 2. The hydrogen atom, the halogen atom, and the ring are also encompassed in the concept of "substituent".

In the present invention, in the case where "m" represents 2 or 3, a plurality of $R^3$ may be the same or different.

The case wherein "m" represents 0 means absence of $R^3$.

The term "IKKβ inhibitor" means one capable of exhibiting a pharmaceutical action by inhibiting IKKβ. Examples of a disease considered to be associated with IKKβ include inflammatory diseases, autoimmune diseases, allergic diseases, infectious diseases, degenerative diseases, vascular diseases, nerve/sensory organ diseases, endocrine/metabolic disease, neoplastic diseases, congenital diseases, traumatic diseases, and adverse reactions after organ transplantation. Specific examples include keratitis, conjunctivitis, uveitis, osteoarthritis, chronic obstructive pulmonary disease, bronchitis, pneumonia, hepatitis, pancreatitis, nephritis, sepsis, systemic inflammatory response syndrome, rheumatoid arthritis, psoriasis, multiple sclerosis, Crohn's disease, ulcerative colitis, systemic erythematosus, Sjogren's syndrome, multiple myositis, dermatomyositis, asthma, allergic rhinitis, hives, atopic dermatitis, age-related macular degeneration, retinopathy of prematurity, polypoidal choroidal vasculopathy, retinal vein occlusion, diabetes and its complication (diabetic retinopathy, diabetic macular edema, diabetic neuropathy, diabetic nephropathy), leukemia, multiple myeloma, malignant lymphoma, solid cancer, cachexia, Alzheimer's disease, Parkinson's syndrome, cerebral infarction, cerebral apoplexy, glaucoma, acquired immune deficiency syndrome, osteoporosis, obesity, fibrosis, gout, fever, headache, acute/chronic pain, hypertension, hyperlipidemia, arteriosclerosis, cardiac infarct, angina, dystrophia, acute respiratory distress syndrome, and the like.

The above specific diseases are described for better understanding of the present invention and not for limiting the scope of the present invention, and there is no particularly limitation on diseases insofar as the diseases are considered to be associated with IKKβ. Also, IKKβ is deeply linked with the transcription factor NF-κB and cytokine production (TNF, IL-1, IL-6, etc.), and diseases considered to be associated with these factors are included in the diseases considered to be associated with IKKβ of the present invention.

In the present compound, the term "salt" is not particularly limited insofar as the salt is pharmaceutically acceptable, and examples of the salt include a salt with an inorganic acid such as hydrochloric acid, hydrobromic acid, hydroiodic acid, nitric acid, sulfuric acid, or phosphoric acid, a salt with an organic acid such as acetic acid, fumaric acid, maleic acid, succinic acid, citric acid, tartaric acid, adipic acid, gluconic acid, glucoheptic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannin acid, trifluoromethanesulfonic acid, benzenesulfonic acid, p-toluenesulfonic acid, lauryl ester sulfate, methyl sulfate, naphthalenesulfonic acid, or sulfosalicylic acid, a quaternary ammonium salt with methyl bromide, methyl iodide, and the like, a salt with a halogen ion such as a bromine ion, a chlorine ion, or an iodine ion, a salt with an alkali metal such as lithium, sodium, or potassium, a salt with an alkali earth metal such as calcium or magnesium, a metal salt with iron, zinc, and the like, a salt with ammonia, a salt with organic amine such as triethylenediamine, 2-aminoethanol, 2,2-iminobis (ethanol), 1-deoxy-1-methylamino-2-D-sorbitol, 2-amino-2-hydroxymethyl-1,3-propanediol, procaine, and N,N-bis(phenylmethyl)-1,2-ethanediamine, or the like.

In the case where a geometric isomer and/or an optical isomer are/is present in the present compound, such isomers are encompassed in the scope of the present invention.

In the case where a hydrate and/or a solvate are/is present in the present compound, such hydrate and/or solvate are/is encompassed in the scope of the present invention.

In the case where there is proton tautomerism in the present compound, the tautomers thereof are also encompassed in the present invention.

In the case where there are crystalline polymorphisms and/or crystalline polymorphism groups (crystalline polymorphism systems) in the present compound, the crystalline polymorphisms and/or crystalline polymorphism groups (crystalline polymorphism systems) thereof are also encompassed in the present invention. Here, the crystalline polymorphism groups (crystalline polymorphism systems) mean individual crystal forms in respective stages when the crystal forms are changed by conditions for the production, crystallization, storage, or the like of the crystals thereof and/or states thereof (the states include also a formulated state) and/or all the processes thereof.

(a) Examples in the present compound include a compound or a salt thereof in which the groups in the compound represented by the general formula (1) or a salt thereof are as described below.

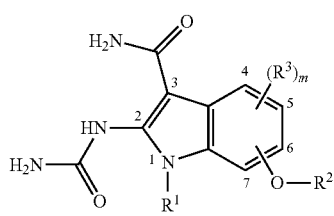

(a1) $R^1$ represents a hydrogen atom, a lower alkyl group which may have a substituent, a hydroxy group, or a lower alkoxy group which may have a substituent; and/or (a2) $R^2$ represents a hydrogen atom, a lower alkyl group which may have a substituent, a lower cycloalkyl group which may have a substituent, an aryl group which may have a substituent, or a heterocyclic group which may have a substituent; and/or (a3) $R^3$ represents a halogen atom, a lower alkyl group which may have a substituent, a lower alkenyl group which may have a substituent, a lower alkynyl group which may have a substituent, a lower cycloalkyl group which may have a substituent, an aryl group which may have a substituent, a heterocyclic group which may have a substituent, a lower alkoxy group which may have a substituent, a lower alkenyloxy group which may have a substituent, a lower alkynyloxy group which may have a substituent, a lower cycloalkyloxy group which may have a substituent, an aryloxy group which may have a substituent, or a heterocyclic oxy group which may have a substituent; and/or (a4) m represents 0, 1, 2, or 3, provided that $R^3$ may be the same or different when m is 2, or 3.

That is, the examples include compounds and salts thereof obtained by combining one or more selected from the above-described (a1), (a2), (a3), and (a4) in the compound represented by the general formula (1).

(b) Preferred examples in the present compound include a compound or a salt thereof in which the groups in the compound represented by the general formula (1) or a salt thereof are as described below.

(b1) $R^1$ represents a hydrogen atom, a lower alkyl group, a hydroxy group, or a lower alkoxy group; and/or (b2) $R^2$ represents a hydrogen atom, a lower alkyl group which may have a substituent, a lower cycloalkyl group, an aryl group which may have a substituent, or a heterocyclic group which may have a substituent; and/or (b3) $R^3$ represents a halogen atom, a lower alkyl group, a lower alkenyl group, a lower alkynyl group, a lower cycloalkyl group, an aryl group, a heterocyclic group, a lower alkoxy group, a lower alkenyloxy group, a lower alkynyloxy group, a lower cycloalkyloxy, an aryloxy group, or a heterocyclic oxy group; and/or (b4) m represents 0, 1, or 2, provided that $R^3$ may be the same or different when m is 2.

That is, the examples include compounds and salts thereof obtained by combining one or more selected from the above-described (b1), (b2), (b3), and (b4) in the compound represented by the general formula (1). Furthermore the selected conditions can be combined with the above condition (a).

(c) Especially preferred examples in the present compound include a compound or a salt thereof in which the groups in the compound represented by the general formula (1) or a salt thereof are as described below.

(c1) $R^1$ represents a hydrogen atom; and/or (c2) $R^2$ represents a hydrogen atom, a lower alkyl group which may have a substituent, an aryl group which may have a substituent, or a heterocyclic group which may have a substituent; and/or (c3) $R^3$ represents a halogen atom, a lower alkenyl group, or a heterocyclic group; and/or (c4) m represents 0, 1, or 2, provided that $R^3$ may be the same or different when m is 2.

That is, the examples include compounds and salts thereof obtained by combining one or more selected from the above-described (c1), (c2), (c3), and (c4) in the compound represented by the general formula (1). Further the selected conditions can be combined with the above conditions (a) and/or (b).

(d) In terms of the binding position of —O—$R^2$ group in the general formula (1), preferred examples of the compounds include those in which the group binds an indole ring at 6-position or a salt thereof. Further the selected conditions can be combined with the above conditions (a), (b) and/or (c).

(e) In terms of m in the general formula (1), preferred examples of the compounds include those in which m represents 0 or a salt thereof. Further the selected conditions can be combined with the above conditions (a), (b) and/or (c).

(f) Particularly preferred specific examples of the present compound include the following compounds and salts thereof.

2-Aminocarbonylamino-6-methoxyindole-3-carboxamide,

2-Aminocarbonylamino-7-methoxyindole-3-carboxamide,

2-Aminocarbonylamino-4-fluoro-7-methoxyindole-3-carboxamide,

2-Aminocarbonylamino-6-hydroxyindole-3-carboxamide,

2-Aminocarbonylamino-6-cyclopropylmethyloxyindole-3-carboxamide,

2-Aminocarbonylamino-6-(4-nitrophenyloxy)indole-3-carboxamide,

2-Aminocarbonylamino-6-(2-chloropyridine-4-yloxy)indole-3-carboxamide,

2-Aminocarbonylamino-6-(2-methyl-4-nitrophenyloxy)indole-3-carboxamide, 6-(4-Acetylaminophenyloxy)-2-(aminocarbonylamino)indole-3-carboxamide, 2-Aminocarbonylamino-4-fluoro-7-methoxy-6-vinylindole-3-carboxamide, 2-Aminocarbonylamino-4-fluoro-6-(furan-3-yl)-7-methoxyindole-3-carboxamide, and 2-Aminocarbonylamino-6-(4-chlorophenyloxy)indole-3-carboxamide.

The present compounds can be prepared according to the following methods. Each specific process for preparing the present compounds is described in detail in the following examples (section of Production Examples). The term "Hal" used in the following synthetic routes represents a halogen atom. $(R)_i$ means an arbitrary substituent represented as $R^3$, and the term "i" represents 0, 1 or 2.

The processes for preparing the present compounds are divided roughly into the methods described bellow, and the suitable method can be chosen according to the kind of substituent.

The present compound (I) can be synthesized according to synthetic route 1. Namely, the present compound (I) can be given by the reaction of the compound (II) with trichloroacetyl isocyanate in an organic solvent such as tetrahydrofuran (hereinafter referred to as "THF") or N,N-dimethylformamide (hereinafter referred to as "DMF") at −80° C. to room temperature for 1 hour to 3 hours, followed by the treatment with ammonia in methanol solution at 0° C. to room temperature for 1 hour to 24 hours.

Synthetic route 1

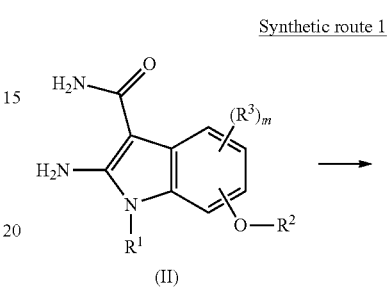

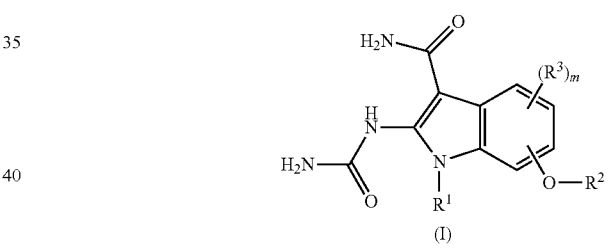

The compound (II)-(a) and the compound (II)-(b) can be synthesized according to synthetic route 2. Namely, the compound (V) can be given by the reaction of the compound (III) with cyanoacetamide (IV) in an organic solvent such as THF or DMF in the presence of a base such as sodium hydride at 0° C. to 80° C. for 1 hour to 24 hours. The compound (II)-(a) and the compound (II)-(b) can be given by the treatment of the obtainable compound (V) with metal powder such as iron or zinc, and acetic acid in an organic solvent such as toluene at room temperature to 100° C. for 30 minutes to 3 hours.

Further, the compound (VI) can be given by the treatment of the compound (V) in an organic solvent such as methanol or DMF in the presence of palladium on carbon under hydrogen atmosphere at room temperature to 60° C. for 1 hour to 24 hours, or by the treatment of the compound (V) with sodium dithionite in aqueous ammonia solution at 0° C. to room temperature for 30 minutes to 24 hours. The compound (II)-(a) can be given by the reaction of the obtainable compound (VI) in an organic solvent such as 1,4-dioxane or DMF at room temperature to 150° C. for 1 hour to 24 hours.

Synthetic route 2

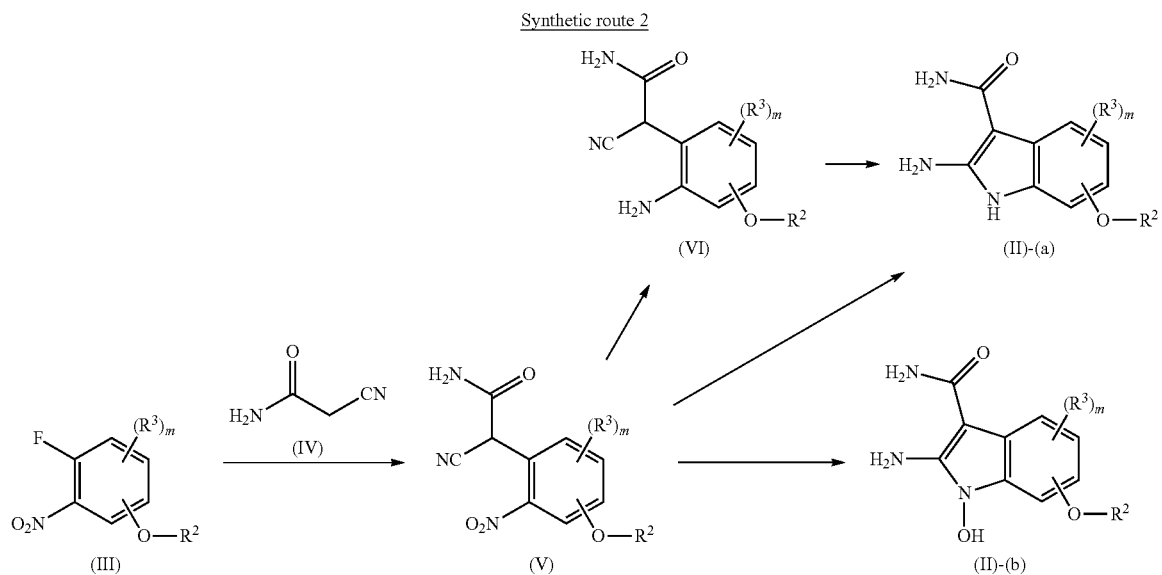

Further, the compound (II)-(a) can be synthesized by a method similar to that described "Journal of Heterocyclic Chemistry, 44, 419-424 (2007)" according to synthetic route 3. Namely, the compound (IX) can be given by the reaction of hydroxylamine (VII) ($Y^a$ represents acetyl or benzoyl group) with malononitrile (VIII) in an organic solvent such as chloroform or THF in the presence of a base such as triethylamine at 0° C. to 80° C. for 1 hour to 6 hours. The compound (II)-(a) can be given by the treatment of the obtainable compound (IX) in an organic solvent such as methanol in the presence of a base such as sodium methoxide or triethylamine at room temperature to 80° C. for 30 minutes to 3 hours.

The compound (VII) can be synthesized according to synthetic route 4. Namely, the compound (XI) can be given by the treatment of the compound (X) in an organic solvent such as THF or ethanol in the presence of hydrazine monohydrate and palladium on carbon at 0° C. to room temperature for 30 minutes to 24 hours. The compound (VII) can be given by the reaction of the obtainable compound (XI) with acetyl chloride or benzoyl chloride (XII) in an organic solvent such as THF or DMF in the presence of a base such as triethylamine or potassium carbonate at 0° C. to 50° C. for 1 hour to 24 hours.

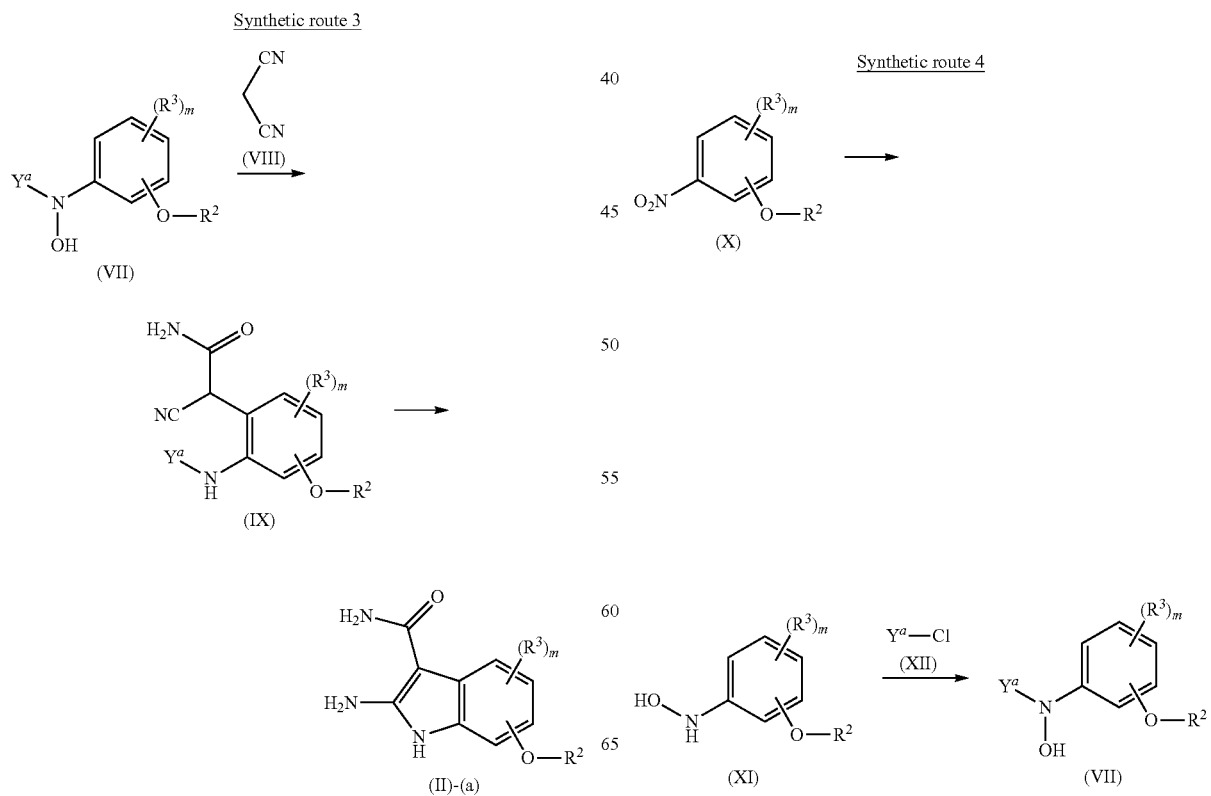

The compound (II)-(c) can be synthesized according to synthetic route 5. ($R^1$ represents a lower alkyl group which may have a substituent.) Namely, the compound (II)-(c) can be given by the reaction of the compound (II)-(a) with alkyl halide (XIII) in an organic solvent such as THF or DMF in the presence of a base such as sodium hydride at 0° C. to 100° C. for 1 hour to 24 hours.

Synthetic route 5

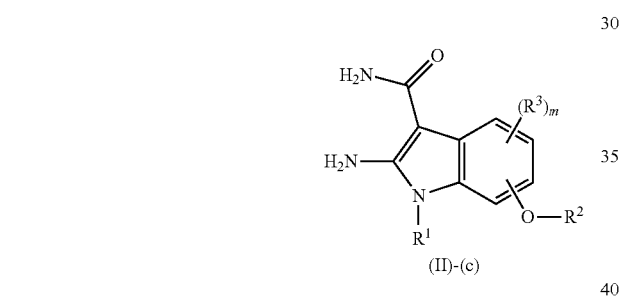

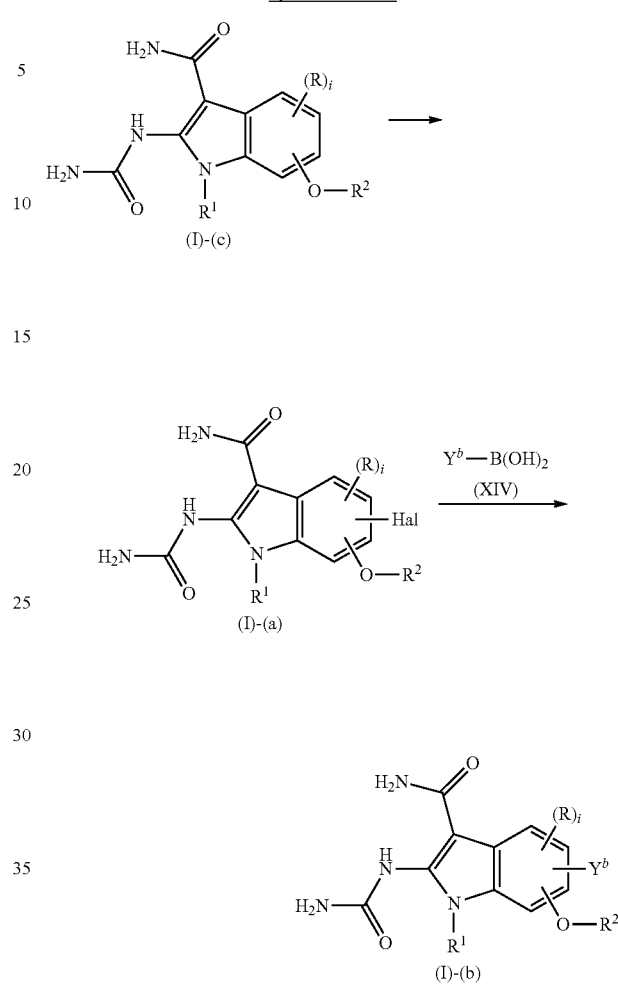

Synthetic route 6

The present compound (I)-(a) and the present compound (I)-(b) can be synthesized according to synthetic route 6. ($Y^b$ represents an aryl group which may have a substituent, or a heterocyclic group which may have a substituent.) Namely, the present compound (I)-(a) can be given by the reaction of the present compound (I)-(c) with a halogenating reagent such as N-bromosuccinimide or N-chlorosuccinimide in an organic solvent such as DMF at 0° C. to 100° C. for 1 hour to 24 hours. The present compound (I)-(b) can be given by the reaction of the present compound (I)-(a) with a boronic acid (XIV) in a mixed solvent, which consists of an organic solvent such as 1,4-dioxane or DMF, and water, in the presence of a metal complex catalyst such as tetrakis(triphenylphosphine)palladium(O) or tris(dibenzylideneacetone)dipalladium(O) and in the presence of a base such as sodium hydrogen carbonate or triethylamine at room temperature to 150° C. for 1 hour to 24 hours.

The present compound (I)-(d), the present compound (I)-(e) and the present compound (I)-(f) can be synthesized according to synthetic route 7. ($Y^c$ represents a lower alkyl group which may have substituent group.) Namely, the present compound (I)-(d) can be given by the reaction of the present compound (I)-(a) with a 1-alkyne (XV) in a mixed solvent, which consists of an organic solvent such as 1,4-dioxane or DMF, and water, in the presence of a metal complex catalyst such as tetrakis(triphenylphosphine)palladium(O) or tris(dibenzylideneacetone)dipalladium(O), in the presence of a copper salt such as copper(I) iodide or copper(I) bromide and in the presence of a base such as sodium hydrogen carbonate or triethylamine at room temperature to 150° C. for 1 hour to 24 hours. Further, the present compound (I)-(e) can be given by the reaction of the present compound (I)-(a) with a boronic acid ester (XVI) in a mixed solvent, which consists of an organic solvent such as 1,4-dioxane or DMF, and water, in the presence of a metal complex catalyst such as tetrakis(triphenylphosphine)palladium(O) or tris(dibenzylideneacetone)dipalladium(O) and in the presence of a base such as sodium hydrogen carbonate or triethylamine at room temperature to 150° C. for 1 hour to 24 hours. Further, the present compound (I)-(f) can be given by the treatment of the present compound (I)-(d) or the present compound (I)-(e) in an organic solvent such as methanol or DMF in the presence of palladium on carbon under hydrogen atmosphere at room temperature to 100° C. for 1 hour to 24 hours.

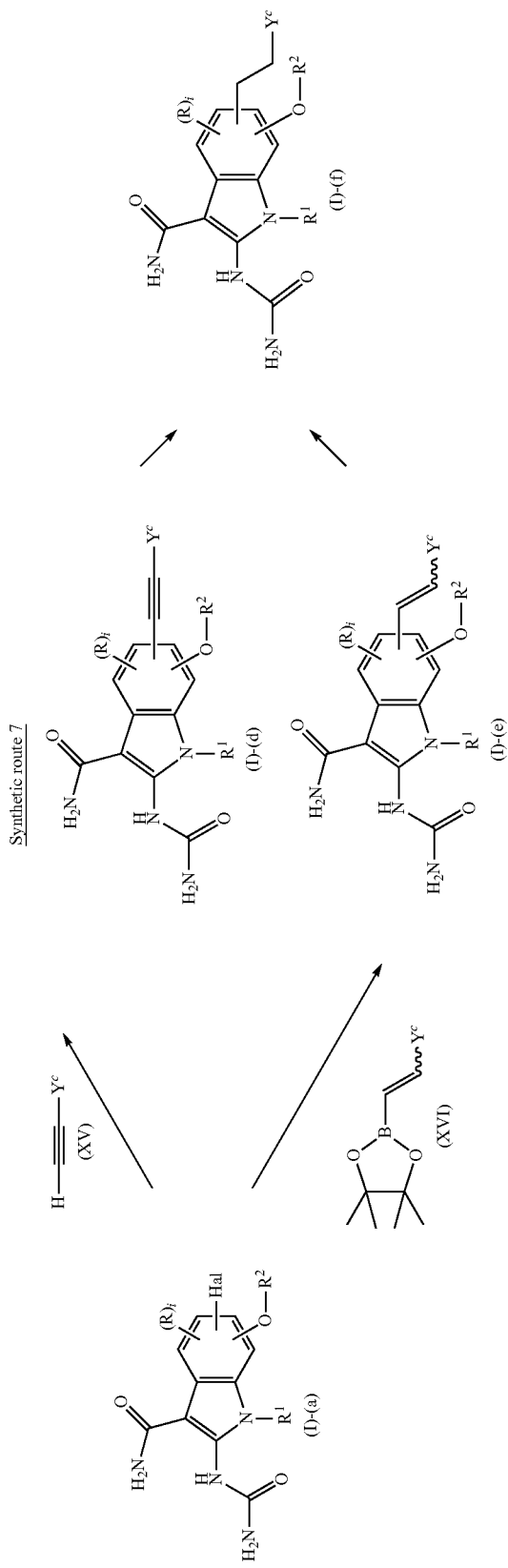

The present compound (I)-(g) and the present compound (I)-(h) can be synthesized according to synthetic route 8. Namely, the present compound (I)-(g) can be given by the treatment of the present compound (I)-(i) in an organic solvent such as dichloromethane in the presence of a Lewis acid such as boron tribromide at −80° C. to room temperature for 1 hour to 24 hours. The present compound (I)-(h) can be given by the reaction of the obtainable present compound (I)-(g) with a halide (XVII) in an organic solvent such as THF or DMF in the presence of a base such as potassium carbonate or sodium hydride at 0° C. to 100° C. for 1 hour to 24 hours. ($R^2$ represents a lower alkyl group which may have a substituent, an aryl group which may have a substituent, or a heterocyclic group which may a have substituent.) Further, the present compound (I)-(h) can be given by the reaction of the present compound (I)-(g) with an alcohol (XVIII) in an organic solvent such as THF or DMF in the presence of a phosphine such as triphenylphosphine or tributylphosphine and a reagent such as diethyl azodicarboxylate or 1,1'-(azodicarbonyl)dipiperidine at 0° C. to 100° C. for 1 hour to 24 hours.

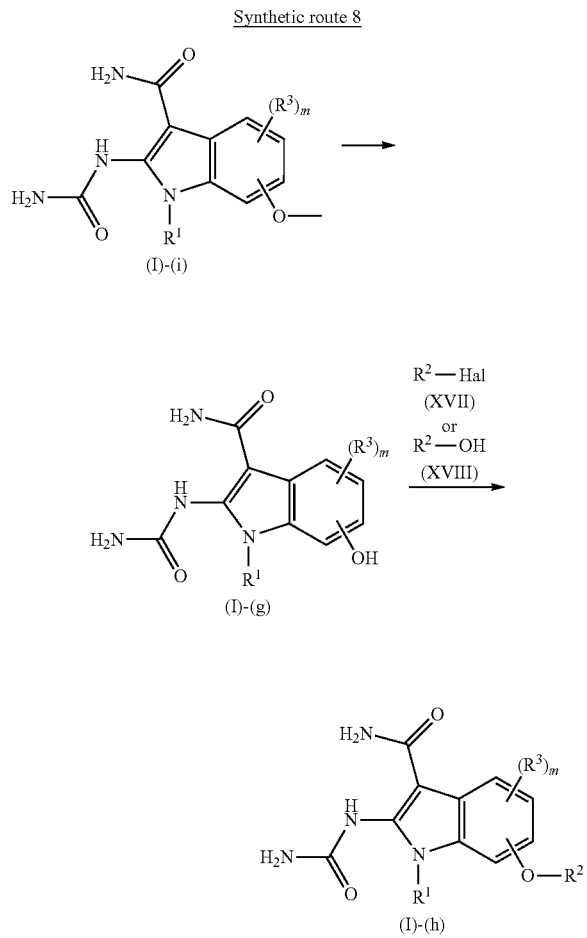

The present compound prepared by the above synthetic routes can be also converted into the above-mentioned salt, hydrate or solvate using widely used techniques.

Details of the above will be described in detail in [Pharmacological Test] in Examples described below in this specification. IKKβ inhibition assay by fluorescence polarization was performed using IMAP™ IKKβ assay kit (manufactured by Molecular Devices Corporation, catalogue No. R8115) or IMAP™ FP Screening Express kit (manufactured by Molecular Devices Corporation, catalogue No. R8127). As a result, the present compound exhibited an excellent IKKβ inhibitory activity.

As described above, IKKβ is involved in outbreak of various diseases, and the present compound having the excellent IKKβ inhibitory activity is useful as an IKKβ inhibitor, and/or a preventive and/or therapeutic agent for the diseases considered to be associated with IKKβ. They are especially useful as a preventive and/or therapeutic agent for inflammatory diseases, autoimmune diseases, allergic diseases, infectious diseases, degenerative diseases, vascular diseases, nerve/sensory organ diseases, endocrine/metabolic disease, neoplastic diseases, congenital diseases, traumatic diseases, and adverse reactions after organ transplantation, and specific examples of such diseases include keratitis, conjunctivitis, uveitis, osteoarthritis, chronic obstructive pulmonary disease, bronchitis, pneumonia, hepatitis, pancreatitis, nephritis, sepsis, systemic inflammatory response syndrome, rheumatoid arthritis, psoriasis, multiple sclerosis, Crohn's disease, ulcerative colitis, systemic erythematosus, Sjogren's syndrome, multiple myositis, dermatomyositis, asthma, allergic rhinitis, hives, atopic dermatitis, age-related macular degeneration, retinopathy of prematurity, polypoidal choroidal vasculopathy, retinal vein occlusion, diabetes and its complication (diabetic retinopathy, diabetic macular edema, diabetic neuropathy, diabetic nephropathy), leukemia, multiple myeloma, malignant lymphoma, solid cancer, cachexia, Alzheimer's disease, Parkinson's syndrome, cerebral infarction, cerebral apoplexy, glaucoma, acquired immune deficiency syndrome, osteoporosis, obesity, fibrosis, gout, fever, headache, acute/chronic pain, hypertension, hyperlipidemia, arteriosclerosis, cardiac infarct, angina, dystrophia, acute respiratory distress syndrome, and the like, more specifically keratitis, conjunctivitis, uveitis, rheumatoid arthritis, age-related macular degeneration, diabetic retinopathy, diabetic macular edema and/or glaucoma.

The present compound can be administered either orally or parenterally. Examples of a dosage form include a tablet, a capsule, a granule, a powder, an injection, an eye drop, a suppository, a percutaneous absorption agent, an ointment, an airsol (including an inhalant), and the like, and these may be prepared by widely used techniques.

For example, an oral preparation such as a tablet, a capsule, a granule, or a powder can be prepared by optionally adding a necessary amount of an excipient such as lactose, mannitol, starch, crystalline cellulose, light silicic anhydride, calcium carbonate, or calcium hydrogen phosphate; a lubricant such as stearic acid, magnesium stearate, or talc; a binder such as starch, hydroxypropyl cellulose, hydroxypropylmethyl cellulose, or polyvinylpyrrolidone; a disintegrant such as carboxymethyl cellulose, low-substituted hydroxypropylmethyl cellulose, or calcium citrate; a coating agent such as hydroxypropylmethyl cellulose, macrogol, or a silicone resin; a stabilizer such as ethyl parahydroxybenzoate or benzyl alcohol; a corrigent such as a sweetener, a sour agent, or a flavor, or the like.

Further, a parenteral preparation such as an injection or an eye drop can be prepared by optionally adding a necessary amount of a tonicity agent such as sodium chloride, concentrated glycerin, propylene glycol, polyethylene glycol, potassium chloride, sorbitol, or mannitol; a buffer such as sodium phosphate, sodium hydrogen phosphate, sodium acetate, citric acid, glacial acetic acid, or trometamol; a surfactant such as polyosorbate 80, polyoxy 40 stearate, or polyoxyethylene hydrogenated castor oil 60; a stabilizer such as sodium citrate or sodium edetate; a preservative such as benzalkonium chloride, paraben, benzethonium chloride, parahydroxybenzoic acid ester, sodium benzoate, or chlorobutanol; a pH adjusting agent such as hydrochloric acid, citric acid, phosphoric acid, glacial acetic acid, sodium hydroxide, sodium carbonate, or sodium hydrogen carbonate; a soothing agent such as benzyl alcohol, or the like.

The dose of the present compound can be appropriately selected depending on the symptoms, age, dosage form, or the like. For example, in the case of an oral preparation, it can be administered in an amount of generally from 0.01 to 1000 mg, preferably from 1 to 100 mg per day in a single dose or several divided doses. In the case of an eye drop, a preparation containing the present compound at a concentration of generally from 0.0001 to 10% (w/v), preferably from 0.01 to 5% (w/v) can be administered in a single dose or several divided doses.

Hereinafter, Production Examples of the present compound, Preparation Examples and results of Pharmacological Tests will be described. However, these examples are described for the purpose of understanding the invention better and are not meant to limit the scope of the invention.

PRODUCTION EXAMPLES

Reference Example 1

N-Acetyl-N-(3-methoxyphenyl)hydroxylamine
(Reference compound No.1-1)

Under ice-cooling, 10% palladium on activated carbon (0.46 g) and hydrazine monohydrate (4.9 mL, 100 mmol) were added to a solution of 3-nitroanisole (7.7 g, 50 mmol) in tetrahydrofuran-ethanol solution (1:1, 100 mL), stirred for 3 hours at room temperature, and let stand overnight at about 5° C. The whole was filtered with celite with ethanol (100 mL), and the filtrate was concentrated under reduced pressure. Sodium hydrogen carbonate (13 g, 150 mmol) and anhydrous N,N-dimethylformamide (50 mL) were added to the obtained residue. Moreover under ice-cooling, acetyl chloride (5.4 mL, 76 mmol) was added thereto and the mixture was stirred for 1 hour. The reaction solution was diluted with water (200 mL) and extracted with ethyl acetate (300 mL×1, 200 mL×1). The combined organic layer was washed with brine (100 mL×2) and dried over anhydrous magnesium sulfate. The solvent was removed under reduced pressure and the residue was purified by silica gel column chromatograpy to give the title reference compound (9.3 g) as an orange oil (quantitative yield)

| N-Acetyl-N-(3-methoxy-phenyl)hydroxylamine (Reference compound No. 1-1) 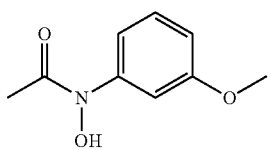 | $^1$H-NMR (500 MHz, DMSO-d$_6$) δ 2.19 (s, 3H), 3.74 (s, 3H), 6.73 (dd, J = 8.6, 1.8 Hz, 1H), 7.18-7.31 (m, 3H), 10.59 (s, 1H) |
|---|---|

As described below, using commercially available compounds, reference compound No.1-2 and 1-3 were obtained by a method similar to reference compound No.1-1.

| N-Acetyl-N-(2-methoxy-phenyl)hydroxylamine (Reference compound No. 1-2) 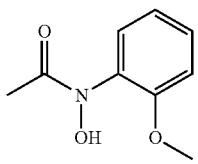 | $^1$H-NMR (400 MHz, DMSO-d$_6$) δ 2 .08 (s, 3H), 3.79 (s, 3H), 6.98 (t, J = 7.4 Hz, 1H), 7.10 (d, J = 7.4 Hz, 1H), 7.26 (d, J = 7.4 Hz, 1H), 7.35 (t, J = 7.4 Hz, 1H), 10.29 (br s, 1H) |
|---|---|
| N-Acetyl-N-(5-fluoro-2-methoxy-phenyl)hydroxylamine (Reference compound No. 1-3) 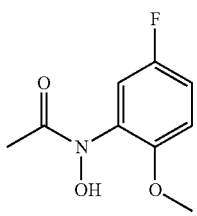 | $^1$H-NMR (500 MHz, DMSO-d$_6$) δ 2.02 (s, 3H), 3.78 (s, 3H), 7.05-7.29 (m, 3H), 10.31 (br s, 1H) |

Reference Example 2

2-Amino-6-methoxyindole-carboxamide (Reference compound No.2-1)

2-Amino-4-methoxyindole-3-carboxamide
(Reference compound No. 2-2)

Triethylamine (7.0 mL, 50 mmol) was added to a solution of N-acetyl-N-(3-methoxyphenyl)hydroxylamine (Reference compound No.1-1, 9.3 g, 50 mmol) and malononitrile (3.4 g, 51 mmol) in chloroform (130 mL), and the mixture was stirred at room temperature for 5 hours. The precipitated solid was filtered off, washed with chloroform (50 mL), and dried at 40° C. under reduced pressure. Anhydrous ethanol (100 mL) and 28% sodium methoxide in methanol solution (20 mL) were added to the obtained solid, and the mixture was stirred for 5 hours at reflux. Under cooling at room temperature, the reaction solution was concentrated in vacuo, diluted with water (300 mL), extracted with ethyl acetate (300 mL). The organic layer was washed with brine (100 mL), dried over anhydrous magnesium sulfate. The solvent was removed under reduced pressure, the obtained solid was filtered off and washed with chloroform-methanol solution (20:1, 200 mL). The solid was dried at 40° C. under reduced pressure to give the title reference compound No.2-1 (2.4 g) as a gray solid (23%). The filtrate was concentrated in vacuo, and the residue was purified by silica gel column chromatography to give the title reference compound No.2-2 (1.3 g) as a brown solid (13%).

| Compound | NMR |
|---|---|
| 2-Amino-6-methoxyindole-3-carboxamide (Reference compound No. 2-1) 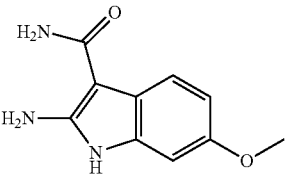 | ¹H-NMR (500 MHz, DMSO-d₆) δ 3.71 (s, 3H), 6.36 (s, 2H), 6.56 (dd, J = 8.6, 2.1 Hz, 1H), 6.66 (s, 2H), 6.72 (d, J = 2.1 Hz, 1H), 7.40 (d, J = 8.6 Hz, 1H), 10.41 (s, 1H) |
| 2-Amino-4-methoxyindole-3-carboxamide (Reference compound No. 2-2) 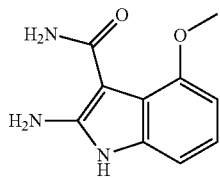 | ¹H-NMR (400 MHz, DMSO-d₆) δ 3.87 (s, 3H), 6.45 (s, 1H), 6.60 (dd, J = 7.0, 2.1 Hz, 1H), 6.79-6.86 (m, 2H), 6.92 (s, 2H), 8.02 (s, 1H), 10.64 (s, 1H) |

As described below, using reference compound No.1-2 or 1-3, reference compound No.2-3 and 2-4 were obtained by a method similar to reference compound No.2-1.

| Compound | NMR |
|---|---|
| 2-Amino-7-methoxyindole-3-carboxamide (Reference compound No. 2-3) 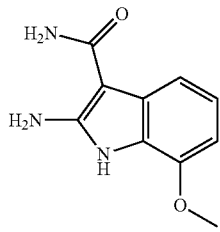 | ¹H-NMR (400 MHz, DMSO-d₆) δ 3.86 (s, 3H), 6.40 (s, 2H), 6.42 (s, 2H), 6.54 (d, J = 7.9 Hz, 1H), 6.87 (t, J = 7.9 Hz, 1H), 7.16 (d, J = 7.9 Hz, 1H), 10.59 (s, 1H) |
| 2-Amino-4-fluoro-7-methoxyindole-3-carboxamide (Reference compound No. 2-4) 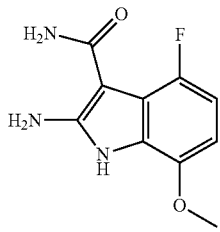 | ¹H-NMR (400 MHz, DMSO-d₆) δ 3.85 (s, 3H), 6.50 (dd, J = 8.7, 3.5 Hz, 1H), 6.61 (br s, 2H), 6.63 (br s, 2H), 6.70 (dd, J = 13.1, 8.7 Hz, 1H), 10.95 (s, 1H) |

Example 1

2-Aminocarbonylamino-6-methoxyindole-3-carboxamide (Compound No.1-1)

Trichloroacetyl isocyanate (1.7 mL, 14 mmol) was added dropwide to a solution of 2-amino-6-methoxyindole-3-carboxamide (Reference compound No.2-1, 2.9 g, 14 mmol) in anhydrous tetrahydrofuran (50 mL) at −40° C. over a period of 10 minutes and the mixture was stirred for 2.5 hours. Moreover, 2.0 M ammonia in methanol solution (40 mL, 80 mmol) was added thereto and the mixture was stirred overnight at room temperature. The reaction solution was concentrated in vacuo, and the obtained solid was filtered off and washed with a mixed solvent of chloroform-methanol (50 mL). The solid was dried at 40° C. under reduced pressure to give the title compound (3.1 g) as a gray solid (88%).

| Compound | NMR |
|---|---|
| 2-Aminocarbonylamino-6-methoxyindole-3-carboxamide (Compound No. 1-1) 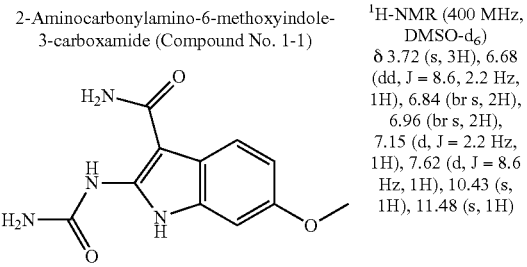 | ¹H-NMR (400 MHz, DMSO-d₆) δ 3.72 (s, 3H), 6.68 (dd, J = 8.6, 2.2 Hz, 1H), 6.84 (br s, 2H), 6.96 (br s, 2H), 7.15 (d, J = 2.2 Hz, 1H), 7.62 (d, J = 8.6 Hz, 1H), 10.43 (s, 1H), 11.48 (s, 1H) |

As described below, using reference compound No.2-2~2-4, compound No-2~1-4 were obtained by a method similar to compound No.1-1.

| Compound | NMR |
|---|---|
| 2-Aminocarbonylamino-4-methoxyindole-3-carboxamide (Compound No. 1-2) 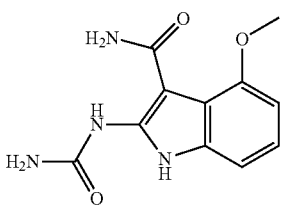 | ¹H-NMR (500 MHz, DMSO-d₆) δ 3.92 (s, 3H), 6.69 (d, J = 7.9 Hz, 1H), 6.79-7.12 (m, 4H), 7.24 (dd, J = 7.9, 0.8 Hz, 1H), 8.32 (s, 1H), 11.11 (s, 1H), 11.71 (s, 1H) |
| 2-Aminocarbonylamino-7-methoxyindole-3-carboxamide (Compound No. 1-3) 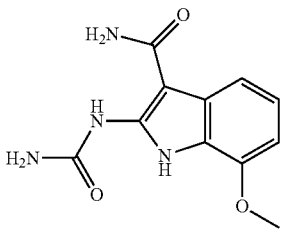 | ¹H-NMR (500 MHz, DMSO-d₆) δ 3.91 (s, 3H), 6.69 (d, J = 7.9 Hz, 1H), 6.94 (br s, 3H), 7.02 (t, J = 7.9 Hz, 1H), 7.16 (br s, 1H), 7.40 (d, J = 7.9 Hz, 1H), 10.36 (s, 1H), 11.09 (s, 1H) |
| 2-Aminocarbonylamino-4-fluoro-7-methoxyindole-3-carboxamide (Compound No. 1-4) 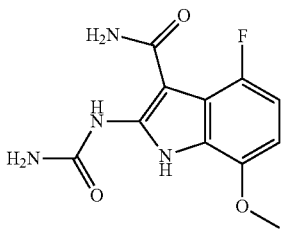 | ¹H-NMR (400 MHz, DMSO-d₆) δ 3.90 (s, 3H), 6.65 (dd, J = 8.8, 3.4 Hz, 1H), 6.76 (br s, 2H), 6.87 (dd, J = 13.1, 8.8 Hz, 1H), 7.27 (br s, 2H), 10.60 (s, 1H), 11.36 (s, 1H) |

Example 2

2-Aminocarbonylamino-6-hydroxyindole-3-carboxamide (Compound No.2-1)

1.0M boron tribromide in dichloromethane solution (4 mL, 45 mmol) was added dropwise to a suspension of 2-Aminocarbonyl amino-6-methoxyindole-3-carboxamide (Compound No.1-1, 3.6g. 15 mmol) in anhydrous dichloromethane (50 mL) over a period of 45 minutes at −70° C. and the mixture was stirred for 1 hour. Moreover, the whole was stirred at −40° C. for 4 hours, then stirred for 1.5 hours under ice-cooling, and water (100 mL) was added thereto. The precipitated solid was filtered off, washed with water (50 mL) and chloroform (50 mL). The solid was dried at 50° C. for 2 hours under reduced pressure to give the title compound (2.7 g) as a brown solid (78%).

| 2-Aminocarbonylamino-6-hydroxyindole-3-carboxamide (Compound No. 2-1) | $^1$H-NMR (400 MHz, DMSO-$d_6$) δ 6.53 (dd, J = 8.5, 2.4 Hz, 1H), 6.76 (br s, 4H), 6.94 (d, J = 2.4 Hz, 1H), 7.49 (d, J = 8.5 Hz, 1H), 8.85 (s, 1H), 10.41 (s, 1H), 11.34 (s, 1H) |
|---|---|
| 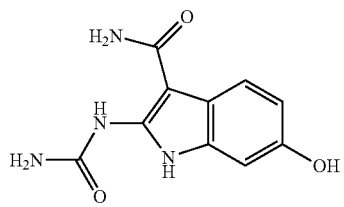 | |

As described below, using compound No.1-2, compound No.2-2 was obtained by a method similar to compound No.2-1.

| 2-Aminocarbonylamino-4-hydroxyindole-3-carboxamide (Compound No. 2-2) | $^1$H-NMR (500 MHz, DMSO-$d_6$) δ 6.49 (dd, J = 7.8, 0.8 Hz, 1H), 6.81 (t, J = 7.8 Hz, 1H), 6.92 (br s, 2H), 7.04 (dd, J = 7.8, 0.8 Hz, 1H), 7.86 (br s, 2H), 10.45 (s, 1H), 10.89 (s, 1H), 11.54 (s, 1H) |
|---|---|
| 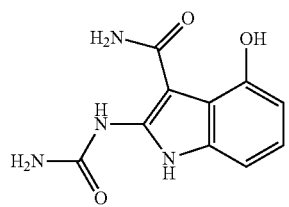 | |

Example 3

2-Aminocarbonylamino-6-propoxyindole-3-carboxamide (Compound No.3-1)

Under ice-cooling, 1-propanol (60 μL, 0.80 mmol), n-tributylphosphine (100 μL, 0.40 mmol) and 1,1'-(azodicarbonyl)dipiperidine (98 mg, 0.39 mmol) were added to a suspension of 2-aminocarbonylamino-6-hydroxyindole-3-carboxamide (Compound No.2-1, 47 mg, 0.20 mmol) in anhydrous tetrahydrofuran (2 mL) and stirred for 2.5 hours. Moreover the whole was stirred overnight at room temperature, and stirred at 50° C. for 7 hours. The reaction solution was purified by silica gel column chromatography to give the title compound (7 mg) as a green solid (13%).

| 2-Aminocarbonylamino-6-propoxyindole-3-carboxamide (Compound No. 3-1) | $^1$H-NMR (400 MHz, DMSO-$d_6$) δ 0.99 (t, J = 7.4 Hz, 3H), 1.66-1.80 (m, 2H), 3.88 (t, J = 6.6 Hz, 2H), 6.67 (dd, J = 8.6, 2.4 Hz, 1H), 6.83 (br s, 2H), 6.96 (br s, 2H), 7.13 (d, J = 2.4 Hz, 1H), 7.60 (d, J = 8.6 Hz, 1H), 10.43 (s, 1H), 11.46 (s, 1H) |
|---|---|
| 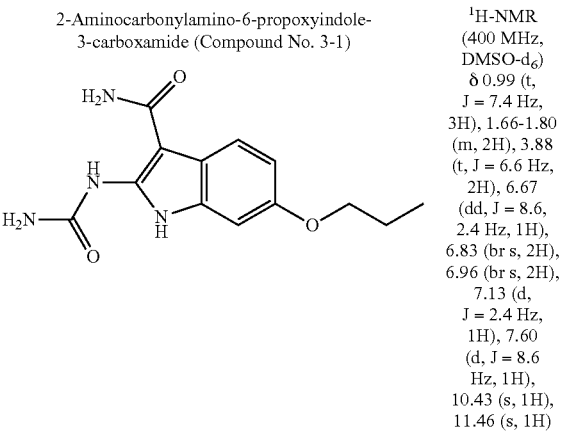 | |

As described below, using commercially available compounds and compound No.2-1, compound No.3-2 was obtained by a method similar to compound No.3-1.

| 2-Aminocarbonylamino-6-cyclopropyl-methyloxyindole-3-carboxamide (Compound No. 3-2) | $^1$H-NMR (500 MHz, DMSO-$d_6$) δ 0.30-0.34 (m, 2H), 0.54-0.59 (m, 2H), 0.88-0.93 (m, 1H), 3.76 (d, J = 7.0 Hz, 2H), 6.67 (dd, J = 8.6, 2.4 Hz, 1H), 6.82 (s, 2H), 6.94 (br s, 2H), 7.12 (d, J = 2.4 Hz, 1H), 7.60 (d, J = 8.6 Hz, 1H), 10.43 (s, 1H), 11.45 (s, 1H). |
|---|---|
| 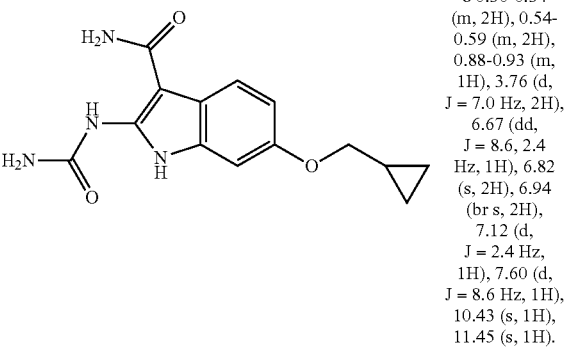 | |

Example 4

2-Aminocarbonylamino-6-(4-nitrophenyloxy)indole-3-carboxamide (Compound No.4-1)

Under ice-cooling, 2-aminocarbonylamino-6-hydroxyindole-3-carboxamide (Compound No.2-1, 1.3 g, 5.5 mmol) in anhydrous N,N-dimethylformamide (7 mL) was added dropwise to a suspension of 60% sodium hydride (450 mg, 11 mmol) in anhydrous N,N-dimethylformamide (15 mL) over a period of 5 minutes and the mixture was stirred for 5 minutes. Moreover 4-fluoronitrobenzene (640 μL, 6.0 mmol) was added thereto, and the mixture was stirred for 15 minutes at room temperature and stirred overnight at 60° C. After cooling, the reaction solution was diluted with water (300 mL) and extracted with ethyl acetate (200 mL). The organic layer was washed with saturated aqueous sodium hydrogen carbonate (200 mL) and brine (200 mL), and dried over anhydrous magnesium sulfate. The solvent was removed under reduced pressure, and the obtained solid was filtered off and washed with a mixed solvent of chloroform-diethyl ether solution (1:2, 60 mL). The solid was dried at 40° C. for 1 hour under reduced pressure to give the title compound (1.2 g) as a brown solid (59%).

| Compound | NMR |
|---|---|
| 2-Aminocarbonylamino-6-(4-nitrophenyloxy)indole-3-carboxamide (Compound No. 4-1) 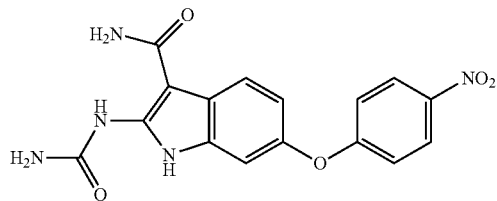 | $^1$H-NMR (500 MHz, DMSO-$d_6$) δ 6.87 (dd, J = 8.6, 2.1 Hz, 1H), 6.99 (br s, 4H), 7.08 (dd, J = 7.1, 2.2 Hz, 2H), 7.36 (d, J = 2.1 Hz, 1H), 7.84 (d, J = 8.6 Hz, 1H), 8.23 (dd, J = 7.1, 2.2 Hz, 2H), 10.52 (s, 1H), 11.79 (s, 1H) |

As described below, using commercially available compounds and compound No.2-1, compound No.4-2~4-7 were obtained by a method similar to compound No.4-1.

| Compound | NMR |
|---|---|
| 2-Aminocarbonylamino-6-(pyrimidine-2-yloxy)indole-3-carboxamide (Compound No. 4-2) 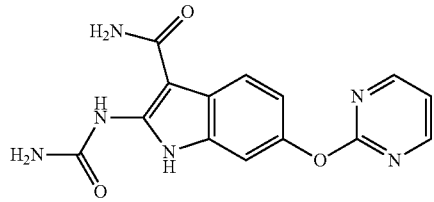 | $^1$H-NMR (400 MHz, DMSO-$d_6$) δ 6.85 (dd, J = 8.8, 2.2 Hz, 1H), 6.95 (br s, 4H), 7.23 (t, J = 4.6 Hz, 1H), 7.32 (d, J = 2.2 Hz, 1H), 7.74 (d, J = 8.8 Hz, 1H), 8.61 (d, J = 4.6 Hz, 2H), 10.50 (s, 1H), 11.70 (s, 1H) |
| 2-Aminocarbonylamino-6-(2-chloropyridine-4-yloxy)indole-3-carboxamide (Compound No. 4-3) 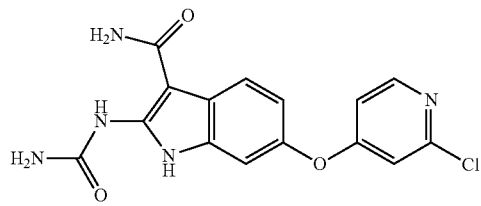 | $^1$H-NMR (500 MHz, DMSO-$d_6$) δ 6.89 (dd, J = 8.6, 2.4 Hz, 1H), 6.91-6.94 (m, 2H), 6.99 (br s, 4H), 7.36 (d, J = 2.4 Hz, 1H), 7.83 (d, J = 8.6 Hz, 1H), 8.26 (dd, J = 5.2, 1.2 Hz, 1H), 10.51 (s, 1H), 11.80 (s, 1H) |
| 2-Aminocarbonylamino-6-(3-methoxy-4-nitrophenyloxy)indole-3-carboxamide (Compound No. 4-4) 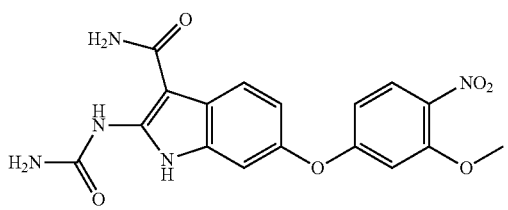 | $^1$H-NMR (400 MHz, DMSO-$d_6$) δ 3.88 (s, 3H), 6.44 (dd, J = 9.0, 2.4 Hz, 1H), 6.87 (dd, J = 8.5, 2.4 Hz, 1H), 6.95 (d, J = 2.4 Hz, 1H), 6.98 (br s, 4H), 7.36 (d, J = 2.4 Hz, 1H), 7.82 (d, J = 8.5 Hz, 1H), 7.95 (d, J = 9.0 Hz, 1H), 10.51 (s, 1H), 11.77 (s, 1H) |

2-Aminocarbonylamino-6-(3-methyl-4-nitrophenyloxy)indole-3-carboxamide
(Compound No. 4-5)

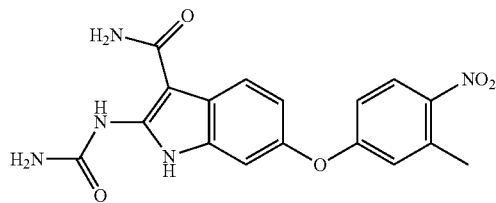

¹H-NMR (400 MHz, DMSO-d₆)
δ 2.50 (s, 3H), 6.78-7.10 (m, 7H), 7.34 (d, J = 2.4 Hz, 1H), 7.82 (d, J = 8.5 Hz, 1H), 8.06 (d, J = 9.0 Hz, 1H), 10.51 (s, 1H), 11.77 (s, 1H)

2-Aminocarbonylamino-6-(2-methyl-4-nitrophenyloxy)indole-3-carboxamide
(Compound No. 4-6)

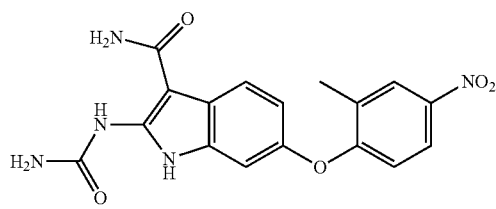

¹H-NMR (400 MHz, DMSO-d₆)
δ 2.42 (s, 3H), 6.73 (d, J = 9.0 Hz, 1H), 6.84 (dd, J = 8.5, 2.2 Hz, 1H), 6.98 (br s, 4H), 7.32 (d, J = 2.4 Hz, 1H), 7.82 (d, J = 8.5 Hz, 1H), 8.02 (dd, J = 9.0, 2.4 Hz, 1H), 8.23 (d, J = 2.2 Hz, 1H), 10.52 (s, 1H), 11.77 (s, 1H)

2-Aminocarbonylamino-6-(2-chloro-4-nitrophenyloxy)indole-3-carboxamide
(Compound No. 4-7)

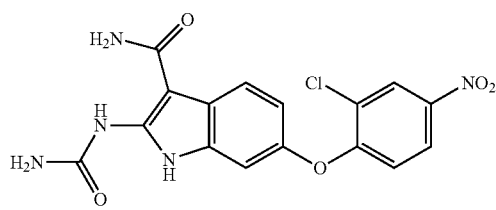

¹H-NMR (400 MHz, DMSO-d₆)
δ 6.90 (dd, J = 8.5, 2.2 Hz, 1H), 6.91 (d, J = 9.0 Hz, 1H), 7.00 (br s, 4H), 7.36 (d, J = 2.2 Hz, 1H), 7.86 (d, J = 8.5 Hz, 1H), 8.14 (dd, J = 9.0, 2.9 Hz, 1H), 8.45 (d, J = 2.9 Hz, 1H), 10.53 (s, 1H), 11.82 (s, 1H)

Example 5

2-Aminocarbonyl amino-6-(4-aminophenyloxy)indole-3-carboxamide (Compound No.5-1)

10% palladium on activated carbon (0.06 g) was added to a suspension of 2-aminocarbonylamino-6-(4-nitrophenyloxy)indole-3-carboxamide (Compound No.4-1, 250 mg, 0.70 mmol) in methanol (7 mL) and the mixture was stirred overnight under hydrogen atmosphere at room temperature. N,N-Dimethylformamide (3 mL) was added thereto, the insoluble matter was filtered out, and the filtrate was concetrated under reduced pressure. Water (30 mL) was added thereto, the precipitated solid was filtered off and washed with water (20 mL). The solid was dried at 40° C. for 1 hour under reduced pressure to give the title compound (100 mg) as a brown solid (44%).

| 2-Aminocarbonylamino-6-(4-aminophenyloxy)indole-3-carboxamide (Compound No. 5-1) | $^1$H-NMR (400 MHz, DMSO-$d_6$) δ 4.87 (s, 2H), 6.56 (dd, J = 6.6, 2.2 Hz, 2H), 6.65 (dd, J = 8.6, 2.2 Hz, 1H), 6.71 (dd, J = 6.6, 2.2 Hz, 2H), 6.87 (br s, 2H), 6.95 (br s, 2H), 7.11 (d, J = 2.2 Hz, 1H), 7.64 (d, J = 8.6 Hz, 1H), 10.44 (s, 1H), 11.54 (s, 1H) |
|---|---|
| 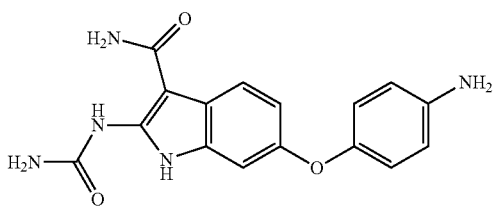 | |

Example 6

6-(4-Acetylaminophenyloxy)-2-(aminocarbonylamino)indole-3-carboxamide (Compound No.6-1)

The solution of 2-aminocarbonylamino-6-(4-aminophenyloxy)indole-3-carboxamide (Compound No.5-1, 40 mg, 0.12 mmol), acetic acid (8 μL, 0.14 mmol), N,N-diisopropylethylamine (46 μL, 0.26 mmol) and O-(7-azabenzotriazol-1-yl)-N,N,N',N'-tetramethyluronium hexafluorophosphate (48 mg, 0.13 mmol) in anhydrous N,N-dimethylformamide (1 mL) was stirred overnight at room temperature. Water (10 mL) was added to the reaction solution, and the precipitated solid was filtered off and washed with water (10 mL). The solid was dried at 40° C. under reduced pressure to give the title compound (21 mg) as a purple solid (46%).

| 6-(4-Acetylaminophenyloxy)-2-(aminocarbonylamino)indole-3-carboxamide (Compound No. 6-1) | $^1$H-NMR (400 MHz, DMSO-$d_6$) δ 2.02 (s, 3H), 6.73 (dd, J = 8.6, 2.4 Hz, 1H), 6.89 (d, J = 9.0 Hz, 2H), 6.91 (br s, 4H), 7.21 (d, J = 2.4 Hz, 1H), 7.53 (d, J = 9.0 Hz, 2H), 7.71 (d, J = 8.6 Hz, 1H), 9.88 (s, 1H), 10.47 (s, 1H), 11.63 (s, 1H) |
|---|---|
| 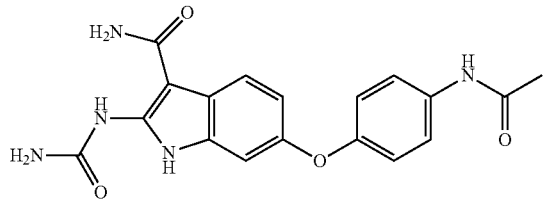 | |

As described below, using commercially available compounds and compound No.5-1, compound No.6-2 was obtained by a method similar to compound No.6-1.

| 2-Aminocarbonylamino-6-(4-methoxy-methylcarbonylaminophenyloxy)indole-3-carboxamide (Compound No. 6-2) | ¹H-NMR (400 MHz, DMSO-d₆) δ 3.37 (s, 3H), 3.98 (s, 2H), 6.74 (dd, J = 8.5, 2.4 Hz, 1H), 6.90 (d, J = 8.8 Hz, 2H), 6.92 (br s, 4H), 7.22 (d, J = 2.4 Hz, 1H), 7.62 (d, J = 8.8 Hz, 2H), 7.72 (d, J = 8.5 Hz, 1H), 9.72 (s, 1H), 10.47 (s, 1H), 11.64 (s, 1H) |
|---|---|
| 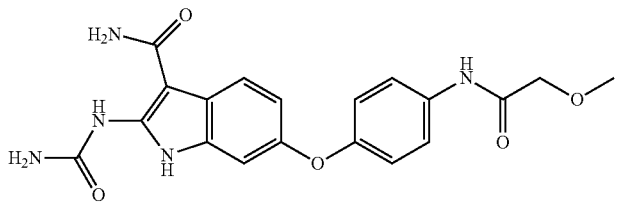 | |

Example 7

2-Aminocarbonylamino-5-bromo-6-methoxyindole-3-carboxamide (Compound No.7-1)

Under ice-cooling, a solution of N-bromosuccinimide (94 mg, 0.53 mmol) in anhydrous N,N-dimethylformamide (1 mL) was added to a solution of 2-aminocarbonylamino-6-methoxyindole-3-carboxamide (Compound No.1-1, 126 mg, 0.51 mmol) in anhydrous N,N-dimethylformamide (1.5 mL) and the mixture was stirred for 1.5 hours. Moreover the whole was stirred for 2 hours at room temperature and stirred for 3 hours at 50° C. After the reaction solution was diluted with water (60 mL) and extracted with ethyl acetate (50 mL), the organic layer was washed with brine (50 mL) and dried over anhydrous magnesium sulfate. After the solvent was removed under reduced pressure, the obtained solid was filtered off and washed with a mixed solvent of diethyl ether-chloroform solution (5:1, 24 mL). The solid was dried at 40° C. under reduced pressure to give the title compound (50 mg) as a gray solid (30%).

| 2-Aminocarbonylamino-5-bromo-6-methoxyindole-3-carboxamide (Compound No. 7-1) | ¹H-NMR (500 MHz, DMSO-d₆) δ 3.78 (s, 3H), 6.93 (br s, 4H), 7.34 (s, 1H), 7.95 (s, 1H), 10.44 (s, 1H), 11.65 (s, 1H) |
|---|---|
|  | |

As described below, using compound No.1-4, compound No.7-2 was obtained by a method similar to compound No.7-1.

| 2-Aminocarbonylamino-6-bromo-4-fluoro-7-methoxyindole-3-carboxamide (Compound No. 7-2) | ¹H-NMR (500 MHz, DMSO-d₆) δ 3.88 (s, 3H), 6.73 (br s, 2H), 7.20 (d, J = 11.9 Hz, 1H), 7.34 (br s, 2H), 10.55 (s, 1H), 11.60 (s, 1H) |
|---|---|
| 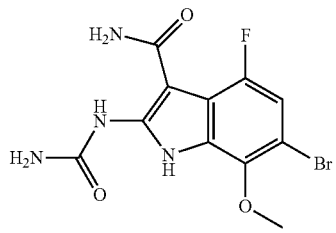 | |

Example 8

2-Aminocarbonylamino-6-methoxy-5-vinylindole-3-carboxamide (Compound No.8-1)

A suspension of 2-aminocarbonylamino-5-bromo-6-methoxyindole-3-carboxamide (Compound No.7-1, 86 mg, 0.26 mmol), vinylboronic acid pinacol ester (121 µL, 0.40 mmol), tetrakis(triphenylphosphine)palladium(0) (32 mg, 0.027 mmol) and sodium hydrogen carbonate (56 mg, 0.66 mmol) in 1,4-dioxane-water solution (3:1, 15 mL) was stirred overnight at 110° C. under argon atmosphere. After cooling, ethyl acetate (20 mL) and brine (15 mL) were added and separated. The organic layer was dried over anhydrous magnesium sulfate and the solvent was removed under reduced pressure. The residue was purified by silica gel column chromatography to give the title compound (4 mg) as a dark green solid (6%).

| 2-Aminocarbonylamino-6-methoxy-5-vinylindole-3-carboxamide (Compound No. 8-1) | ¹H-NMR (500 MHz, DMSO-d₆) δ 3.76 (s, 3H), 5.12 (dd, J = 11.3, 1.8 Hz, 1H), 5.92 (dd, J = 17.7, 1.8 Hz, 1H), 6.84 (br s, 2H), 6.94 (s, 2H), 7.00 (dd, J = 17.7, 11.3 Hz, 1H), 7.20 (s, 1H), 7.80 (s, 1H), 10.48 (s, 1H), 11.52 (s, 1H). |
|---|---|
| 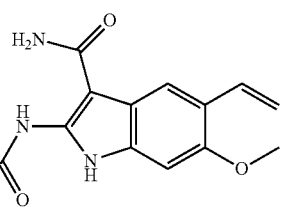 | |

As described below, using commercially available compounds and compound No.7-2, compound No.8-2 and 8-3 were obtained by a method similar to compound No.8-1.

| 2-Aminocarbonylamino-4-fluoro-7-methoxy-6-vinylindole-3-carboxamide (Compound No. 8-2) | ¹H-NMR (400 MHz, DMSO-d₆) δ 3.81 (s, 3H), 5.30 (d, J = 11.2 Hz, 1H), 5.84 (d, J = 17.6 Hz, 1H), 6.74 (br s, 2H), 6.94 (dd, J = 17.6, 11.2 Hz, 1H), 7.20 (d, J = 14.2 Hz, 1H), 7.32 (br s, 2H), 10.58 (s, 1H), 11.50 (s, 1H) |
|---|---|
| 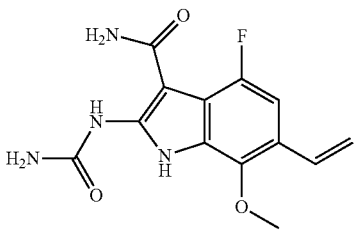 | |

| 2-Aminocarbonylamino-4-fluoro-6-(furan-3-yl)-7-methoxyindole-3-carboxamide (Compound No. 8-3) | $^1$H-NMR (400 MHz, DMSO-$d_6$) δ 3.76 (s, 3H), 6.75 (br s, 2H), 7.05 (dd, J = 1.7, 0.8 Hz, 1H), 7.23 (d, J = 14.2 Hz, 1H), 7.32 (br s, 2H), 7.77 (t, J = 1.7 Hz, 1H), 8.17 (dd, J = 1.7, 0.8 Hz, 1H), 10.59 (s, 1H), 11.54 (s, 1H) |
|---|---|

Example 9

2-Aminocarbonylamino-6-(4-chlorophenyloxy)indole-3-carboxamide (Compound No.9-1)

Under ice-cooling, a solution of sodium nitrite (42 mg, 0.61 mmol) in water (400 μL) was added to a suspension of 2-aminocarbonylamino-6-(4-aminophenyloxy) indole-3-carboxamide (Compound No.5-1, 99 mg, 0.30 mmol) in anhydrous dichloromethane (2 mL) and 6N hydrochloric acid (4 mL) and the mixture was stirred for 2 hours. Moreover a solution of copper(I) chloride (162 mg, 1.6 mmol) in concentrated hydrochloric acid (500 μL) was added thereto and the mixture was stirred 30 minutes. The whole was stirred overnight at room temperature. The reaction solution was diluted with water (30 mL) and methanol (20 mL), extracted with ethyl acetate (100 mL). The organic layer was washed with brine (100 mL) and dried over anhydrous magnesium sulfate. After the solvent was removed under reduced pressure, the residue was purified by silica gel column chromatography to give the title compound (9 mg) as a brown solid (8%).

| 2-Aminocarbonylamino-6-(4-chlorophenyloxy)indole-3-carboxamide (Compound No. 9-1) | $^1$H-NMR (400 MHz, DMSO-$d_6$) δ 6.78 (dd, J = 8.6, 2.4 Hz, 1H), 6.94 (dd, J = 6.7, 2.3 Hz, 2H), 7.05 (br s, 4H), 7.26 (d, J = 2.4 Hz, 1H), 7.38 (dd, J = 6.7, 2.3 Hz, 2H), 7.76 (d, J = 8.6 Hz, 1H), 10.49 (s, 1H), 11.70 (s, 1H) |
|---|---|

Further, commercially available compounds are compounds listed on product catalogs published by Sigma-Ardrich, Wako Pure Chemical Industries Ltd., Kanto Chemical Co., Inc., Tokyo Chemical Industry Co., Ltd., Nacalai Tesque Inc., and so on from 2006 to 2008.

Preparation Examples

Hereinafter, typical preparation examples of the present compound will be described.

1) Tablet (in 150 mg)

| Present compound | 1 mg |
|---|---|
| Lactose | 100 mg |
| Cornstarch | 40 mg |
| Carxboxymethyl cellulose calcium | 4.5 mg |
| Hydroxypropyl cellulose | 4 mg |
| Magnesium stearate | 0.5 mg |

A tablet of the above-mentioned formulation is coated using 3 mg of a coating agent (for example, a conventional coating agent such as hydroxypropylmethyl cellulose, macrogol, a silicone resin or the like), whereby an objective tablet can be obtained. In addition, a desired tablet can be also obtained by appropriately changing the type and/or amount of the present compound and additives.

2) Capsule (in 150 mg)

| Present compound | 5 mg |
|---|---|
| Lactose | 135 mg |
| Carboxymethylcellulose Calcium | 4.5 mg |
| Hydroxypropyl Cellulose | 4 mg |
| Magnesium Stearate | 1.5 mg |

A desired capsule can be obtained by appropriately changing the type and/or amount of the present compound and additives 3) Eye drop (in 100 ml)

| Present compound | 100 mg |
|---|---|
| Sodium chloride | 900 mg |
| Polysorbate 80 | 500 mg |
| Sodium hydroxide | q.s. |
| Hydrochloric acid | q.s. |
| Sterile purified water | q.s. |

A desired eye drop can be obtained by appropriately changing the type and/or amount of the present compound and additives.

[Pharmacological Test]

1. IKKβ Inhibitory Activity Measurement Test

In order to evaluate IKKβ inhibitory activity of the present compounds, an IKKβ inhibition assay by a fluorescence polarization method was conducted. The assay was conducted using IMAP™ IKKβ assay kit (manufactured by Molecular Devices Corporation, catalogue No. R8115) or IMAP™ FP Screening Express kit (manufactured by Molecular Devices Corporation, catalogue No. R8127) in accordance with the protocol attached to each kit. The specific methods are described below.

(Preparation of Reagents)

1) Complete Reaction Buffer: a complete reaction buffer was so prepared to obtain a final composition of 10 mM Tris-HCL (pH 7.2), 10 mM magnesium chloride, 0.1% bovine serum albumin, and 1 mM dithiothreitol.

2) Substrate Working Solution: 400 nM substrate working solution was prepared by dissolving and diluting a fluorescein-labeled IKKβ substrate peptide (amino acid sequence: GRHDSGLDSMK) with the complete reaction buffer.

3) Enzyme Working Solution: 0.2 units/mL enzyme working solution was prepared by diluting IKKβ solution (manufactured by Upstate Biotechnology Inc., catalogue No. 14-485) with the complete reaction buffer.

4) ATP Working Solution: 8 μM ATP working solution was prepared by dissolving ATP into ultrapure water followed by diluting it with the complete reaction buffer.

5) IMAP binding solution: After diluting an IMAP binding buffer with ultrapure water, an IMAP binding solution was prepared by diluting an IMAP binding reagent with the diluted IMAP binding buffer.

(Preparation of Test Compound Solution)

A test compound was dissolved in dimethyisulfoxide followed by diluting it with the complete reaction buffer to prepare 4 μM test compound solution.

(Test Method and Measurement Method)

1) To a 384-well plate, the test compound solution, the enzyme working solution, the substrate working solution, and the ATP working solution were added in an amount of 5 μL per well.

2) Incubation was performed at room temperature for 60 minutes under light shielding.

3) The IMAP binding solution was added in an amount of 60 μL per well.

4) Incubation was performed at room temperature for 30 minutes under light shielding.

5) Fluorescence polarization value of each well was measured by using Analyst™ HT (multimode plate reader manufactured by Molecular Devices Corporation) and Criterion Host Software v2.00 (manufactured by Molecular Devices Corporation).

6) Operations were performed in the same manner as in 1) to 5) except for changing the test compound to 0.4% dimethylsulfoxide. The obtained result was designated as a control.

7) Operations were performed in the same manner as in 1) to 5) except for changing the test compound and the enzyme working solution to 0.4% dimethylsulfoxide and the complete reaction buffer, respectively. The obtained result was designated as a background.

(Calculation Equation for IKKβ Inhibition Rate)

An IKKβ inhibition rate (%) was calculated by the following equation.

IKKβ inhibition rate (%)=100×{1-(fluorescence polarization value of test compound−fluorescence polarization value of background)/(fluorescence polarization value of control−fluorescence polarization value of background)}

(Evaluation Results)

As examples of evaluation results, IKKβ inhibition rates (%) of the test compounds (Compound No.1-1, 1-3, 1-4, 2-1, 3-2, 4-1, 4-3, 4-6, 6-1, 8-2, 8-3, and 9-1) at 1 μM are shown in Table I.

TABLE I

|  | IKKβ Inhibition Rate (%) |
|---|---|
| Compound No. 1-1 | 95 |
| Compound No. 1-3 | 78 |
| Compound No. 1-4 | 60 |
| Compound No. 2-1 | 90 |
| Compound No. 3-2 | 91 |
| Compound No. 4-1 | 100 |
| Compound No. 4-3 | 89 |
| Compound No. 4-6 | 97 |
| Compound No. 6-1 | 98 |
| Compound No. 8-2 | 91 |
| Compound No. 8-3 | 87 |
| Compound No. 9-1 | 92 |

IKKβ inhibition rate exceeding 100% is indicated as 100%.

As shown in Table I, the present compounds exhibited the excellent IKKβ inhibition rates. Therefore, the present compounds can be used as an IKKβ inhibitor and useful as a preventive and/or therapeutic agent for the diseases considered to be associated with IKKβ, such as inflammatory diseases, autoimmune diseases, allergic diseases, infectious diseases, degenerative diseases, vascular diseases, nerve/sensory organ diseases, endocrine/metabolic disease, neoplastic diseases, congenital diseases, traumatic diseases, or adverse reactions after organ transplantation.

The invention claimed is:

1. A compound represented by the following formula (1) or a salt thereof:

, wherein $R^1$ represents a hydrogen atom, a lower alkyl group which may have a substituent, a hydroxy group, or a lower alkoxy group which may have a substituent;

$R^2$ represents a hydrogen atom, a lower alkyl group which may have a substituent, a lower cycloalkyl group which may have a substituent, an aryl group which may have a substituent, or a heterocyclic group which may have a substituent;

$R^3$ represents a halogen atom, a lower alkyl group which may have a substituent, a lower alkenyl group which may have a substituent, a lower alkynyl group which may have a substituent, a lower cycloalkyl group which may have a substituent, an aryl group which may have a substituent, a heterocyclic group which may have a substituent, a lower alkoxy group which may have a substituent, a lower alkenyloxy group which may have a substituent, a lower alkynyloxy group which may have a substituent, a lower cycloalkyloxy group which may have a substituent, an aryloxy group which may have a substituent, or a heterocyclic oxy group which may have a substituent;

m represents 0, 1, 2, or 3, provided that $R^3$ may be the same or different when m is 2, or 3.

2. The compound or a salt thereof according to claim 1, wherein, in the formula (1), $R^1$ represents a hydrogen atom, a lower alkyl group, a hydroxy group, or a lower alkoxy group;

$R^2$ represents a hydrogen atom, a lower alkyl group which may have a substituent, a lower cycloalkyl group, an aryl group which may have a substituent, or a heterocyclic group which may have a substituent;

$R^3$ represents a halogen atom, a lower alkyl group, a lower alkenyl group, a lower alkynyl group, a lower cycloalkyl group, an aryl group, a heterocyclic group, a lower alkoxy group, a lower alkenyloxy group, a lower alkynyloxy group, a lower cycloalkyloxy, an aryloxy group, or a heterocyclic oxy group;

m represents 0, 1, or 2, provided that $R^3$ may be the same or different when m is 2.

3. The compound or a salt thereof according to claim 1, wherein, in the formula (1), $R^1$ represents a hydrogen atom;

$R^2$ represents a hydrogen atom, a lower alkyl group which may have a substituent, an aryl group which may have a substituent, or a heterocyclic group which may have a substituent;

$R^3$ represents a halogen atom, a lower alkenyl group, or a heterocyclic group;

m represents 0, 1, or 2, provided that $R^3$ may be the same or different when m is 2.

4. The compound or a salt thereof according to any one of claims 1 to 3, wherein, in the formula (1), —O—$R^2$ binds to indole ring at 6-position.

5. The compound or a salt thereof according to any one of claims 1 to 3, wherein, in the formula (1), m represents 0.

6. A compound or a salt thereof selected from the group consisting of 2-aminocarbonylamino-6-methoxyindole-3-carboxamide, 2-aminocarbonylamino-7-methoxyindole-3-carboxamide, 2-aminocarbonylamino-4-fluoro-7-methoxyindole-3-carboxamide, 2-aminocarbonylamino-6-hydroxyindole-3-carboxamide, 2-aminocarbonylamino-6-cyclopropylmethyloxyindole-3-carboxamide, 2-aminocarbonylamino-6-(4-nitrophenyloxy)indole-3-carboxamide, 2-aminocarbonylamino-6-(2-chloropyridine-4-yloxy) indole-3-carboxamide, 2-aminocarbonylamino-6-(2-methyl-4-nitrophenyloxy) indole-3-carboxamide, 6(4-acetylaminophenyloxy)-2-(aminocarbonylamino)indole-3-carboxamide, 2-aminocarbonylamino-4-fluoro-7-methoxy-6-vinylindole-3-carboxamide, 2-aminocarbonylamino-4-fluoro-6-(furan-3-yl )-7-methoxyindole-3-carboxamide, and 2-aminocarbonylamino-6-(4-chlorophenyloxy)indole-3-carboxamide.

7. A pharmaceutical composition comprising the compound or a salt thereof according to any one of claims 1 to 3 and a pharmaceutical carrier.

8. The pharmaceutical composition according to claim 7, for the treatment of age-related macular degeneration.

9. The pharmaceutical composition according to claim 7, for the treatment of diabetic retinopathy or diabetic macular edema.

10. The pharmaceutical composition according to claim 7, for the treatment of keratitis, conjunctivitis or uveitis.

11. The pharmaceutical composition according to claim 7, for the treatment of glaucoma.

12. The pharmaceutical composition according to claim 7, for the treatment of rheumatoid arthritis.

13. A method for inhibiting IKKβ comprising administering to a patient a pharmaceutically effective amount of the compound or a salt thereof according to any one of claims 1 to 3.

14. A method for treating age-related macular degeneration comprising administering to a patient a therapeutically effective amount of the compound or a salt thereof according to any one of claims 1 to 3.

15. A method for treating diabetic retinopathy or diabetic macular edema comprising administering to a patient a therapeutically effective amount of the compound or a salt thereof according to any one of claims 1 to 3.

16. A method for treating keratitis, conjunctivitis or uveitis comprising administering to a patient a therapeutically effective amount of the compound or a salt thereof according to any one of claims 1 to 3.

17. A method for treating glaucoma comprising administering to a patient a therapeutically effective amount of the compound or a salt thereof according to any one of claims 1 to 3.

18. A method for treating rheumatoid arthritis comprising administering to a patient a therapeutically effective amount of the compound or a salt thereof according to any one of claims 1 to 3.

* * * * *